United States Patent [19]

Haadsma-Svensson et al.

[11] Patent Number: 5,708,018

[45] Date of Patent: Jan. 13, 1998

[54] 2-AMINOINDANS AS SELECTIVE DOPAMINE D3 LIGANDS

[75] Inventors: Susanne R. Haadsma-Svensson, Portage, Mich.; Bengt R. Andersson; Clas A. Sonesson, both of Gothenburg, Sweden; Chiu-Hong Lin, Portage, Mich.; R. Nicholas Waters, Gothenburg, Sweden; Kjell A. I. Svensson, Portage, Mich.; Per A. E. Carlsson; Lars O. Hansson, both of Gothenburg, Sweden; N. Peter Stjernlof, Vastra Frolunda, Sweden

[73] Assignee: Pharmacia & Upjohn Company, Kalamazoo, Mich.

[21] Appl. No.: 592,318

[22] PCT Filed: Jul. 21, 1994

[86] PCT No.: PCT/US94/08046

§ 371 Date: May 14, 1996

§ 102(e) Date: May 14, 1996

[87] PCT Pub. No.: WO95/04713

PCT Pub. Date: Feb. 16, 1995

Related U.S. Application Data

[63] Continuation of Ser. No. 103,270, Aug. 6, 1993, abandoned.

[51] Int. Cl.$^6$ ............... A61K 31/135; A61K 31/165; C07C 211/42; C07C 233/43

[52] U.S. Cl. ............... 514/408; 514/452; 514/463; 514/510; 514/647; 548/578; 549/359; 549/433; 558/46; 558/56; 558/58; 564/308

[58] Field of Search ............... 558/46, 56, 58; 549/359, 433; 548/578; 564/308; 514/408, 452, 463, 510, 647

[56] References Cited

U.S. PATENT DOCUMENTS

| | | | |
|---|---|---|---|
| 4,192,888 | 3/1980 | Bondinell et al. | 424/321 |
| 4,743,618 | 5/1988 | Horn | 514/438 |

FOREIGN PATENT DOCUMENTS

| | | | |
|---|---|---|---|
| 334538 | 9/1989 | European Pat. Off. | |
| 402923 | 12/1990 | European Pat. Off. | |
| 538134 | 4/1993 | European Pat. Off. | |
| 1545673 | 8/1969 | Germany. | |
| 90/07490 | 7/1990 | WIPO | C07C 217/74 |

OTHER PUBLICATIONS

Sundeen, J. E. et al., J. Med. Chem. vol. 20, No. 11, (1977) pp. 1478–1485.

Chemical Abstracts, vol. 81, No. 19, Nov. 1974, abstract No: 1202865.

Chemical Abstracts, vol. 80, No. 21, May 1974, abstract No: 120604y.

S. P. Arneric, et al., Neuropharmacol., 21, (1982), pp. 885–890.

S. P. Arneric, et al. Arch. Int. Pharmacodyn., Ther. 257, (1982), pp. 263–273.

R. K. Bhatnagar, et al., Pharmacol., Biochem. Behav., 17 (Suppl. 1), (1982), pp. 11–19.

Sindelar, et al., J. Med. Chem., 25, (1982), pp. 858–864.

J. G. Cannon, et al., J. Med. Chem., 25, (1982), pp. 1442–1446.

J. G. Cannon, et al., J. Med. Chem., 27, (1984), pp. 186–189.

J. G. Cannon, et al., J. Med. Chem., 28, (1985), pp. 515–518.

J. G. Cannon, et al., J. Med. Chem., 29, (1986), 2016–20.

U. Hacksell, et al., J. Med. Chem., 24, (1981), pp. 429–434.

S. Ma et al., J. Pharmacol. Exp. Ther., 256, (1991), pp. 751–756.

Nichols, D. E., et al., J. Med. Chem., 33, (1990), pp. 703–710.

*Primary Examiner*—Jacqueline Haley
*Attorney, Agent, or Firm*—Donald L. Corneglio

[57] ABSTRACT

Compounds and their pharmaceutically acceptable salts suitable for treating central nervous system disorders associated with the dopamine D3 receptor activity of Formula I:

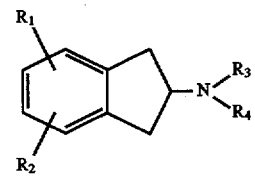

wherein $R_1$ and $R_2$ are independently chosen from hydrogen, $C_1$–$C_8$ alkyl, $OCH_3$, OH, $OSO_2CF_3$, $OSO_2CH_3$, $SOR_5$, $CO_2R_5$, $CONH_2$, $CONR_5R_6$, $COR_5$, CN, $SO_2NH_2$, $SO_2NR_5R_6$, $SO_2R_5$, —OCO—($C_1$–$C_6$ alkyl), —NCO—($C_1$–$C_6$ alkyl), —$CH_2$O—($C_1$–$C_6$ alkyl), —$CH_2$OH, —CO-Aryl, —$NHSO_2$-Aryl, —$NHSO_2$—($C_1$–$C_6$ alkyl), phthalimide, thiophenyl, pyrrol, pyrrolinyl, oxazolyl, or $R_1$ and $R_2$ together form —O(CH$_2$)$_{1-2}$O— or —(CH$_2$)$_{3-6}$— (except that only one of $R_1$ and $R_2$ can be hydrogen or OH in any such compound); $R_3$ and $R_4$ are independently chosen from $C_2$–$C_4$ alkenyl, $C_3$–$C_8$ alkynyl, $C_3$–$C_8$ cycloalkyl, —(CH$_2$)$_p$— thienyl (where p is 1–4), or $C_1$–$C_8$ alkyl (except where $R_1$ or $R_2$ are hydrogen or OH or where both $R_1$ and $R_2$ are $OCH_3$ or a $C_1$–$C_8$ alkyl); $R_5$ is hydrogen, $C_1$–$C_8$ alkyl, $C_2$–$C_4$ alkenyl, $C_3$–$C_8$ cycloalkyl; and $R_6$ is $C_1$–$C_8$ alkyl, $C_2$–$C_4$ alkenyl, $C_2$–$C_8$ alkynyl, $C_3$–$C_8$ cycloalkyl, or Aryl.

8 Claims, No Drawings

2-AMINOINDANS AS SELECTIVE DOPAMINE D3 LIGANDS

This application is the national phase of international application PCT/US94/08046, filed 21 Jul. 1994, which is a continuation of U.S. Ser. No. 08/103,270, filed 6 Aug. 1993 now abandoned.

BACKGROUND OF THE INVENTION

The subject invention is directed toward 2-aminoindan analogs that selectively bind to the dopamine D3 receptor in vitro. The dopamine D3 receptor was recently cloned by Sokoloff et al. (Nature, 347, 146 (1990)). It was hypothesized that this receptor subtype is of importance for the action of anti-psychotics. Interestingly, this receptor shows a high abundance in brain regions associated with emotional and cognitive functions.

Compounds with this profile may be useful in treating CNS disorders, e.g. schizophrenia, mania, depression, geriatric disorders, drug abuse and addiction, Parkinson's disease, anxiety disorders, sleep disorders, circadian rhythm disorders and dementia.

INFORMATION DISCLOSURE STATEMENT

Americ, S. P. et al., Neuropharmacol., 21, 885 (1982) describes indan analogs compared with other dopamine agonists. Compounds with 5,6 substitution were found to be inactive in this model of food intake.

Americ, S. P. et al., Arch. Int. Pharmocodyn. Ther., 257, 263 (1982) describes 2-aminotetralin and 2-aminoindan analogs where the 5,6 dimethoxy substituted compound is again disclosed as inactive agents in an assay to evaluate contractions in vascular smooth muscle.

Bhatnagar, R. K. et al., Pharmacol., Biochem. Behav., 17(Suppl. 1), 11 (1982) discusses SAR studies of various structural entities including aminoindans which interact with dopamine receptors. The 5,6 dimethoxy indans are disclosed as inactive compounds.

Cannon, J. G. et al., J. Med. Chem., 25, 858 (1982) describes 4,7-dimethoxy-2 aminoindans and their dopaminergic and cardiovascular actions.

Cannon, J. G. et al., J. Med. Chem., 25, 1442 (1982) discloses the synthesis of the 5,6 di-methoxy and di-hydroxy indans and also some biology which shows they are devoid of dopamine receptor activity.

Cannon, J. G. et al., J. Med. Chem., 27, 186 (1984) describes the synthesis of N-alkylated derivatives of 2-amino-4,6-dihydroxyindans.

Cannon, J. G. et al., J. Med. Chem., 28, 515 (1985) describes the resolution of the 4-hydroxy aminoindan.

Cannon, J. G. et al., J. Med. Chem., 29, 2016 (1986) describes the ortho OH/methyl, hydroxymethyl, formyl or carboxy derivatives of 2-aminoindans (4,5 substitution), aminotetralins and benz[f]quinolines.

Hacksell, U. et al., J. Med. Chem., 24, 429 (1981) describes the synthesis of monophenolic 2-aminoindans as central dopamine receptor stimulants.

Ma, S. et al., J. Pharmacol. Exp. Ther., 256, 751 (1991) describes dopaminergic structure activity relationships of 2-aminoindans with mainly di-substitution in the 4,5 positions.

Nichols, D. E. et al., J. Med. Chem., 33, 703 (1990) describes noneurotoxic tetralin and indan analogues of 3,4 (methylenedioxy)amphetamine.

PCT Patent Publication No. WO90/07490 describes 2-aminotetralins and 2-aminoindans with aromatic substitution with an $OCH_3$ or $OH$ in conjunction with a Br group.

European Patent 88302599.1 filed Mar. 24, 1988 discloses antiarrhythmic aminoindanes having a bicyclic structure and methyl group on the amine not disclosed in the subject invention.

U.S. Pat. No. 4,132,737 discloses trifluoromethyl substituted 1-aminoindanes whereas the subject invention is 2-aminoindanes.

SUMMARY OF THE INVENTION

In one aspect the subject invention is directed toward compounds and pharmaceutically acceptable salts of Formula I:

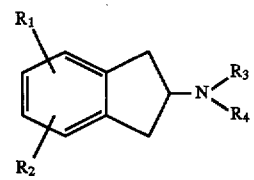

wherein $R_1$ and $R_2$ are independently chosen from hydrogen, $C_1$–$C_8$ alkyl, $OCH_3$, $OH$, $OSO_2CF_3$, $OSO_2CH_3$, $SOR_5$, $CO_2R_5$, $CONH_2$, $CONR_5R_6$, $COR_5$, $CF_3$, $CN$, $SR_5$, $SO_2NH_2$, $SO_2NR_5R_6$, $SO_2R_5$, —OCO—$C_1$–$C_6$ alkyl, —NCO—$C_1$–$C_6$ alkyl, —$CH_2O$—$C_1$–$C_6$ alkyl, —$CH_2OH$, —CO-Aryl, —$NHSO_2$-Aryl, —$NHSO_2$—$C_1$–$C_{15}$ alkyl, phthalimide, thiophenyl, pyrrol, pyrrolinyl, oxazol, halogen (Br, Cl, F, I), $R_6$ or $R_1$ and $R_2$ together form —$O(CH_2)_mO$— (where m is 1–2) or —$CH_2(CH_2)_pCH_2$— (where p is 1–4); (except that only one of $R_1$ and $R_2$ can be hydrogen, $OCH_3$ or $OH$ in any such compound);

$R_3$ and $R_4$ are independently chosen from $C_2$–$C_4$ alkenyl, $C_3$–$C_8$ alkynyl, $C_3$–$C_8$ cycloalkyl, —$(CH_2)_p$-thienyl (where p is 1–4), hydrogen (except that only one of $R_3$ and $R_4$ can be hydrogen in any such compound) or $C_1$–$C_8$ alkyl (except where $R_1$ or $R_2$ are hydrogen, $OCH_3$ or $OH$);

$R_5$ is hydrogen, $C_1$–$C_8$ alkyl, $C_2$–$C_4$ alkenyl, $C_3$–$C_8$ cycloalkyl; and $R_6$ is $C_1$–$C_8$ alkyl, $C_2$–$C_4$ alkenyl, $C2$-$C_8$ alkynyl, $C_3$–$C_8$ cycloalkyl, or Aryl.

In another aspect the subject invention is directed toward compounds and pharmaceutically acceptable salts of Formula I, above, wherein $R_1$ and $R_2$ are independently chosen from hydrogen, $OCH_3$, $OH$, $OSO_2CF_3$, $OSO_2CH_3$, $SOR_5$, $CO_2R_5$, $CONH_2$, $CONR_5R_6$, $COR_5$, $CF_3$, $CN$, $SR_5$, $SO_2NH_2$, $SO_2NR_{SR6}$, $SO_2R_5$, halogen (Br, Cl, F), $R_6$, or $R_1$ and $R_2$ together form —$O(CH_2)_mO$— (where m is 1–2);

$R_3$ and $R_4$ are taken together to form a —$(CR_5R_5)_n$—ring structure bonded to said nitrogen atom where n is 4–8;

$R_5$ is hydrogen, $C_1$–$C_8$ alkyl, $C_2$–$C_4$ alkenyl, $C_3$–$C_8$ cycloalkyl; and $R_6$ is $C_1$–$C_8$ alkyl, $C_2$–$C_4$ alkenyl, $C_2$–$C_8$ alkynyl, $C_3$–$C_8$ cycloalkyl, or Aryl.

In yet another aspect, the subject invention is directed toward a method for treating central nervous system disorders associated with the dopamine D3 receptor activity in a patient in need of such treatment comprising administering to the subject a therapeutically effective amount of a Formula I compound for alleviation of such disorder. Typically, the compound of Formula I is administered in the form of a pharmaceutical composition comprising a pharmaceutically-acceptable carrier or diluent.

In yet another aspect, the subject invention is directed toward a pharmaceutical composition for treating central nervous system disorders associated with the dopamine D3 receptor activity comprising an effective amount of a compound of Formula I with a pharmaceutically-acceptable carrier or diluent.

DETAILED DESCRIPTION OF THE INVENTION

The subject invention is directed toward compounds or pharmaceutically acceptable salts of Formula I as depicted above in either racemic or pure enantiomer forms. $R_1$ and $R_2$ are independently chosen as listed above; except that only one of $R_1$ and $R_2$ can be hydrogen, $OCH_3$ or OH in any such compound to avoid those compounds disclosed in the literature where similar $R_1$ and $R_2$ groups are chosen from hydrogen, $OCH_3$ and OH.

$R_3$ and $R_4$ are independently chosen as listed above except that only one of $R_3$ and $R_4$ can be hydrogen in any such compound to thereby eliminate the possibility of a primary amine being formed. Secondary and tertiary amines are the preferred structure. $R_3$ and $R_4$ can also independently be $C_1$-$C_8$ alkyl except where $R_1$ or $R_2$ are hydrogen, $OCH_3$ or OH in order to avoid similar compounds disclosed in the literature (Hacksell, Cannon).

In a second variation of Formula I, $R_3$ and $R_4$ are taken together to form a —$(CR_5R_5)_n$— ring structure bonded to said nitrogen atom where n is 4–8; thus $R_1$ and $R_2$ can be independently chosen from hydrogen, $OCH_3$, OH, $OSO_2CF_3$, $OSO_2CH_3$, $SOR_5$, $CO_2R_5$, $CONH_2$, $CONR_5R_6$, $COR_5$, $CF_3$, CN, $SR_5$, $SO_2NH_2$, $SO_2NR_5R_6$, $SO_2R_5$, halogen (Br, Cl, F), $R_6$, or $R_1$ and $R_2$ together form —$O(CH_2)_mO$— (where m is 1–2).

"Alkyl" are one to eight carbon atoms such as methyl, ethyl, propyl, butyl, pentyl, hexyl, heptyl, octyl and isomeric forms thereof.

"Aryl" are six to twelve carbon atoms such as phenyl, α-naphthyl, β-naphthyl, m-methylphenyl, p-trifluoromethylphenyl and the like. The aryl groups can also be substituted with one to three hydroxy, fluoro, chloro, or bromo groups.

"Cycloalkyl" are three to eight carbon atoms such as cyclopropyl, cyclobutyl, cyclopentyl and cyclohexyl.

Pharmaceutically acceptable salts include salts of both inorganic and organic acids. The preferred pharmaceutically acceptable salts include salts of the following acids: methanesulfonic, hydrochloric, hydrobromic, sulfuric, phosphoric, nitric, benzoic, citric, tartaric, fumaric or maleic.

The compounds of Formula I are active orally or parenterally. Orally the Formula I compounds can be given in solid dosage forms such as tablets or capsules, or can be given in liquid dosage forms such as elixirs, syrups or suspensions as is known to those skilled in the art. It is preferred that the Formula I compounds be given in solid dosage form and that it be a tablet.

Typically, the compounds of Formula I can be given in the amount of about 0.25 mg to about 100 mg/person, one to three times a day. Preferably, about 10 to about 50 mg/day in divided doses.

The exact dosage and frequency of administration depends on the particular compound of Formula I used, the particular condition being treated, the severity of the condition being treated, the age, weight, general physical condition of the particular patient, other medication the individual may be taking as is well known to those skilled in the art and can be more accurately determined by measuring the blood level or concentration of the active compound in the patient's blood and/or the patient's response to the particular condition being treated.

Thus, the subject compounds, along with a pharmaceutically-acceptable carrier, diluent or buffer, can be administrated in a therapeutic or pharmacological amount effective to alleviate the central nervous system disorder with respect to the physiological condition diagnosed. The compounds can be administered intravenously, intramuscularly, topically, transdermally such as by skin patches, buccally or orally to man or other vertebrates.

The compositions of the present invention can be presented for administration to humans and other vertebrates in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar pharmaceutical diluent or carrier materials. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions, the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The lyophilized powder can then be sealed in the vial and reconstituted prior to use.

Chemical Synthesis:

Chart A. Synthesis of 2-aminotetralin derivatives

Steps 1 and 2. Conversion of the 1-indanone to the oxime (A-1) followed by hydrogenation to the primary amine (A-2) can be performed by methods known in the art.

Step 3. The primary amine is reductively aminated to yield di-substitution (Preparation 7) or coupled with acid to form the amide (Preparation 16). This amide can be in turn reduced, with e.g. LAH. If appropriate, another acylation (Preparation 13) or akylation can take place. The primary amine could also be alkylated with an alkylhalide (preferably, alkylbromide or chloride) under basic conditions to yield N-alkyl or N-azacyclic derivatives.

Step 4. If one or more substituents on the aromatic ring is a methoxygroup, it may be converted to the corresponding phenol (A-4) using 48% HBr or lithium-diphenyl phosphine in THF.

Step 5. Conversion of the phenols to the triflates may be accomplished using methods know in the art such as triflic anhydride in base (Examples 2,3) or N-phenyltriflurormethanesulfonimide (Example 36).

Step 6. A di-triflate derivative (A-5, Example 3) can be convened to the di-carbomethoxy derivative via palladium chemistry (A-6, Example 9, *J. Chem. Soc. Chem. Commun.* 1987, 904). In addition, mono-carbomethoxy mono-hydroxy derivative is obtained in this transformation (A-6, Example 10). This di-triflate can also be convened to mono-hydroxy, mono-triflate by heating with triethylamine in DMF/MeOH (A-6, Example 7). This compound in turn can be converted by acetylation (Ac$_2$O/pyridine) to mono-acetoxy, mono-triflate (A-6, Example 8) and by alkylation (NaH/DMF, MeI) to mono-methoxy, mono-triflate (A-6, Example 56), via the chemistry known in the art. Following the palladium chemistry described above, the mono-acetoxy, mono-triflate (A-6, Example 8) can be converted to mono-acetoxy, mono-carbomethoxy derivative (A-6, Example 54). Usng the simlar chemistry, the mono-methoxy, mono-triflate (A-6, Example 56) can be converted to mono-carbomethoxy, mono-methoxy derivative (A-6, Example 57) and mono-ethynyl, mono-methoxy derivative (A-6, Example 63), as well as to mono-acetyl, mono-methoxy derivative (A-6, Example 61) via the procedure of Example 52. The mono-carbomethoxy, mono-methoxy derivative can be converted to the fromyl derivative by DIBAL-H at low temperaure (A-6, Example 58), or to hydroxymethyl derivative (A-6, Example 59) by LAH, both methods knon in the art. The mono-carbomethoxy, mono-hydroxy derivative (A-6, Example 10) is converted to the mono-carbomethoxy monotriflate derivative (Example 55), following the procedure of preparing di-triflate (Example 3), or basic hydrolysis (NaOH/MeOH-H$_2$O) to mono-carboxy, mono-methoxy derivative (A-6, Example 60). The mono-carbomethoxy, mono-methoxy derivative (A-6, Example 57) can be converted to mono-carboxamido, mono-methoxy derivative (A-6, Example 62) via the procedure of Example 35. This in turn converted to mono-cyano, mono-methoxy derivative via the procedure of Example 53. The di-carbomethoxy derivative (A-6, Example 9) is converted to di-hydroxymethyl derivative (A-6, Example 64) via LAH reduction known in the art and in turn this is converted to di-methoxymethyl derivative (A-6, example 66) via the procedure of Example 56.

Chart B: Synthesis of the Methylene- and Ethylene-Dioxy Analogs

The di-ol (Example A4 from Chart A) is alkylated using bromomethane or dibromoethane in DMF and a base such as K$_2$CO$_3$.

Chart C.

Step 1. An amide (A-3) intermediate (such as Preparation 13) can be converted to the arylbromide (or aryliodide) (C-1) using procedure such as Br$_2$/HOAc which is known in the art (Preparation 14 or 15).

Step 2. Reduction of the arylbromide-amide (C-1) using the reducing agent such as lithium lauminum hydride affords the arylbromide-amine (C-2, Preparation 17.

Step 3. The arylbromide (C-2) is converted to arylfriflurormethyl derivative (C-2) via heating in a mixture of sodium trifluoroacetate, copper (I) iodide, and N-methylpyridone (Example 48, *Chem Lett* 1981,1719). Or the arylbromide (C-2) is lithiated, reacted with sulfur dioxide, followed by sulfuryl chloride treatment and ammonia gas to yield arylsulfonamide (Example 49, *Organomet. Chem. Rev. Sect. A* 1970, 5, 281). The trifluoromethansulfonyloxy dervative (Example 2) can be converted via palladium chemistry to thiophene derivative (C-2, Example 50, *J. Am. Chem. Soc.* 1987, 109, 5478; *Synthesis* 1980, 727), ethynyl derivative (C-2, Example 51, *J. Am. Chem. Soc.* 1987, 109, 5478), or acetyl derivative (C-2, Example 52, *J. Org Chem.* 1990, 55, 3654). The carboxamido derivative (Example 35) also can be converted to the cyano derivative (C-2, Example 53, *J. Med. Chem.* 196811, 322) using POCl$_3$/DMF, a method known in the art.

Chart D.

Step 1. The diamine (from, PCT/US94/02800) can be converted to compounds with a variety of substituents on the aromatic ring (D-1) e.g. Examples 20. 21, 22, 23, 27, 28, 29, and 30.

Step 2. The N-benzyl group can be removed using hydrogenolysis conditions known in the art (see Examples 24) to yield the secondary amines (D-2)

Step 3. The secondary amines can be further converted to the tertiary amine via the condtions described in Step 3, Chart A (as in Example 26).

Chart E: Synthesis of 1-indanones

Step 1: Conversion of a substituted benzaldehyde to the cinnamic acid derivative (E-1) can be achieved by methods known in the art.

Step 2: The cinnamic acid can be reduced using hydrogenation conditions to yield the saturated acid (E-2).

Step 3: The acid is cyclized using Friedel Crafts acylation by one of the various methods known in the art (heating in polyphosphoric acid, or conversion to the acyl chloride followed by cyclization using a Lewis acid such as AlCl$_3$) to yield the substituted 1-indanones (E-3).

Preparation of Intermediates and Specific Examples:

Preparation 1. 5-Methoxy-2-oximino-1-indanone (A-1, Chart A).

This compound was synthesized from 5-methoxy-1-indanone using the procedure outlined in Cannon, J. G. et al., J. Med. Chem., 25, 1442 (1982). Briefly, to a solution of 5-methoxy-1-indanone (500 mg, 3 mmol) in 20 mL methanol at 40° C. was added n-butylnitrite (0.4 mL, 3.4 mmol) followed by 0.3 mL conc. HCl. The solution was stirred for 30 minutes, during which time a white precipitate was formed. The solution was then cooled to 0° C. on an ice bath and the precipitate filtered and dried to yield an off white solid (465 mg, 85%); mp 226°–227° C.

Preparation 2. 5,6 -Dimethoxy-2-oximo-1-indanone (A-1, Chart A).

This compound was prepared as outlined in Cannon, J. G. et al., J. Med. Chem., 25, 1442 (1982).

Preparation 3. 5-Fluoro-2-oximo-1-indanone (A-1, Chart A).

This compound was prepared using the method described in Preparation 1 using 5-fluoro-1-indanone to yield the title compound as a white solid (1.99 g, 84%); mp 204°–206° C.

Preparation 4. 5-Methoxy-2-aminoindan (A-2, Chart A).

This preparation was carried out following the procedure outlined in Cannon, J. G. et al., J. Med. Chem., 25, 1442 (1982). Briefly, to a solution of oxime (Preparation 1) in acetic acid (70 mL) and sulfuric acid (4.9 mL) was added 10% Pd/C and hydrogenated at 50 psi for 6 hours. The reaction mixture was filtered over celite and concentrated. This material was used as is in the following reactions. The amine could also be extracted using chloroform from a basic solution to yield the amine free base as a solid.

Preparation 5. 5,6-Dimethoxy-2-aminoindan (A-2, Chart A).

This compound was prepared using the method described in Preparation 4 using the oximes prepared in Preparation 2.

Preparation 6. 5-Fluoro-2-aminoindan (A-2, Chart A).

This compound was prepared using the method described in Preparation 4 using the oxime prepared in Preparation 3.

Preparation 7. 5-Methoxy-2-(n-propylamino)indan (A-3, Chart A).

To a solution of 5-Methoxy-2-aminoindan (Preparation 4, 4.9 g, 30 mmol) in 1,2 dichloroethane (100 mL) and THF (30 mL) was added TEA to pH 4–5. Propionaldehyde (8.7 mL, 120 mmol) was added followed by sodium triacetoxyborohydride (19.07 g, 90 mmol) in portions. The reaction was concentrated to remove solvents followed by addition of 10% HCl. The solution was basified using 1N NaOH to pH>10 and extracted with ethyl acetate. The combined organic layers were washed with brine, dried, filtered and evaporated to yield a yellow orange solid. This solid was purified by column chromatography using methylene chloride/methanol (19:1) to yield an oil. The oil was converted to the HCl salt and recrystallized using methanol/ethyl acetate; mp 165°–167° C.

Preparation 8. 5,6-dimethoxy-2-(n-propylamino)indan (A-3, Chart A).

The title compound was prepared following the procedure outlined in Preparation 7 using 5,6-dimethoxy-2-aminoindan (Preparation 5) to yield a white solid; mp 210°–213° C.

Preparation 9. 5-Hydroxy-2-(n-propylamino)indan hydrobromide (A-3, Chart A).

A solution of 5-methoxy-2-(n-propylamino)indan (Preparation 7, 1.6 g, 6.5 mmol) in 48% HBr (10 mL) was refluxed at 100° C. overnight. The solution was concentrated to dryness and recrystallized from methanol/ether to yield a light gray solid (1.6 g, 80%) as the hydrobromide salt, 206°–207° C.

Preparation 10. 5,6-dihydroxy-2-(n-propylamino)indan (A-3, Chart A).

The title compound was prepared following the same procedure outlined in Preparation 9 using 5,6-dimethoxy-2-(n-propylamino)indan (Preparation 8) to yield a light gray solid; mp 275°–280° C.

Preparation 11. 5-Methoxy-2-(di-methyl)indan (A-3, Chart A).

The title compound was prepared from 5-Methoxy-2-aminoindan (Preparation 4) using the preparation outlined in Preparation 7 using formaldehyde replacing the propionaldehyde to yield a white solid; mp 206°–207° C.

Preparation 12. 5,6-dimethoxy-2-(di-n-butylamino)indan (A-3, Chart A).

The title compound was prepared from 5,6-dimethoxy-2-aminoindan (preparation 5) using the preparation outlined in Preparation 7 using n-butylaldehyde replacing the propionaldehyde to yield a white solid; mp 142°–143° C.

Preparation 13. 2-N-Indan-2-yl-N-propyl-propionamide. (A-3, Chart A)

To a solution of N-indan-2-yl-propylamine (9.5 g, 54.3 mmol) in methylene chloride was added aq. Na$_2$CO$_3$ (150 mL, 3%) followed by propionyl chloride (7.5 mL, 86.3 mmol). The mixture was stirred at ambient temperature for 1 h. The layers were separated and the organic layer was washed with water, separated and dried (MgSO$_4$). Evaporation of the solvent yielded 7 g (56%) of N-indan-2-yl-N-propyl-propionamide. MS m/e 231 (1, M+), 116 (100), 117 (23), 57 (11), 146 (9).

Preparation 14. N-(6-Bromo-indan-2-yl)-N-propyl-propionamide. (C-1, Chart C)

N-Indan-2-yl-N-propyl-propionamide (Preparation 13, 1 g, 4.32 mmol) was dissolved in dichloromethane (100 mL). Glacial acetic acid was added to adjust the pH to 4. This was followed by the addition of bromine (0.4 ml, 7.78 mmol). The solution was stirred at room temperature for 8 h. Additional bromine (0.2 ml, 3.89 mmol) was added and the solution was refluxed for 18 h. Since the reaction was not complete another portion of bromine (0.2 ml, 3.89 mmol) was added and the reaction mixture was refluxed for another 4 h. The organic layer was extracted with aqueous Na$_2$CO$_3$ (10%) and the layers were separated. The organic layer was dried (MgSO$_4$). The solvent was evaporated and the remaining crude product was chromatographed (SiO$_2$) with n-hexane:ethyl acetate (4:1) as eluant. The pure fractions were pooled yielding 0.45 g (34%) of N-(6-Bromo-indan-2-yl)-N-propyl-propionamide. $^1$H NMR (300 MHz, CDCl$_3$) δ 0.85 (t, 3H), 1.15 (t, 3H), 1.50–1.65 (m, 2H), 2.30–2.50 (m, 2H), 2.90–3.25 (m, 6H), 4.70–5.10 (m, 1H), 7.00–7.10 (t, 1H), 7.25–7.40 (m, 2); MS m/e 309 (1, M+), 116 (100), 115 (92), 194 (57), 196 (55).

Preparation 15. N-(5-Iodo-indan-2-yl)-N-propyl-propionamide and N-(4-Iodo-indan-2-yl)-N-propyl-propionamide. (C-1, Chart C)

N-Indan-2-yl-N-propyl-propion-amide (preparation 13, 210 mg, 0.97 mmol), solid iodine (280 mg, 1.1 mmol) and silver nitrate (190 mg, 1.12 mmole) were dissolved in dichloromethane (30 mL) and stirred for 48 h. Additional iodine (560 mg) and silver nitrate (380 mg) were added and the mixture was stirred for further 72 h. The organic layer was washed with aq. Na$_2$CO$_3$ (10%), dried (MgSO$_4$) and the solvent evaporated to yield a mixture of two regio isomers (ratio 96:4) with similar mass spectra: MS m/e 357 (3, M+), 272 (13), 242 (100), 115 (57), 57 (12).

Preparation 16. 5,6-di-methoxy-2-N-indan-2-yl-propionamide. (A-3, Chart A)

A solution of 5,6-di-methoxy-2-aminoindan (Preparation 5, 700 mg, 3.6 mmol), propionic acid (0.29 mL, 3.98 mmol), triethylamine (0.62 mL, 4.5 mmol) and diethylphosphonate (0.6 mL, 3.98 mmol) in methylene chloride (40 mL) was stirred at rt for 3 h. The solution was concentrated and purified by chromatography on 100 g silica gel eluting with methylene chloride/methanol (45:1) to yield the title compound as an off-white solid (750 mg, 85%): MS m/e 249, 176, 161,146, 133.

Preparation 17. 5,6-di-methoxy-2-(propylamino)indan (A-3, Chart A)

To a suspension of lithium aluminum hydride in THF (10 mL) was added 5,6-di-methoxy-2-N-indan-2-yl-propionamide. (Preparation 16, 750 mg, 3 mmol) in THF (10 mL). The solution was stirred at rt for 3 h, then refluxed for 2 h. The mixture was cooled and 1N NaOH and water added slowly. This mixture was stirred then extracted with ethyl acetate. The organic layers were washed with brine, dried (MgSO$_4$), filtered and evaporated to yield an oil. The oil was chromatographed on 100 g silica gel eluting with methylene chloride/methanol (9:1) to yield the title compound as an oil (600 mg, 85%): MS m/e 235, 220, 206, 178, 166, 151.

Preparation 18. 5,6-di-hydroxy-2-(propylamino)indan (A-5, Chart A)

A solution of 5,6-di-methoxy-2-(propylamino)indan (Preparation 17, 600 mg, 2.5 mmol) in HBr (48%, 5 mL) was refluxed overnight. The reaction mixture was concentrated with ethanol to yield a brown black solid that was used without further purification.

Preparation 19. 4-methyl-2-oximino-1-indanone (A-1, Chart A)

This compound was prepared using the method described in Preparation 1 using 4-methyl-1-indanone (Johnson Mathey Co, lot #J21F) to yield the title compound as a white solid (680 mg, 57%); mp 204° C.

Preparation 20. 4-methyl-2-aminoindan (A-2, Chart A)

The compound was prepared using the method described in Preparation 4 using the oxime prepared in Preparation 19 to yield a yellow oil which was used without further purification.

Preparation 21. 3,4-di-methyl cinnamic acid (E-1, Chart E)

This material was made as described in J. Heterocyclic. Chem., 24, 677 (1987). Briefly, a solution of 3,4-benzaldehyde (5 g, 37.3 mmol) and malonic acid (5.82 g, 56 mmol) in pyridine (15 mL) and piperidine (5 mL) was refluxed (bath temp 120° C.) for 6 h. The reaction was cooled to rt and concentrated HCl added dropwise to pH 1. The resulting precipitate was collected, washed with water and dried to yield a white solid (6.1 g, 93%): mp 171°–172° C.

Preparation 22. 3,4-(dimethylphenyl)propionic acid (E-2, Chart E)

To a solution of 3,4-di-methyl cinnamic acid (Preparation 21, 3.3 g, 18.7 mmol) in methanol (150 mL) was added Pd/C (10%, 330 mg) and hydrogenated at 30 psi for 15 min. The reaction was filtered over celite and the filtrate concentrated to yield the title compound as a white solid (3.1 g, 94%): mp 81°–83° C.

Preparation 23. 6,7-di-methyl-1-indanone and 5,6-di-methyl-1-indanone (E-3, Chart E).

To 3,4-(dimethylphenyl)propionic acid (Preparation 22, 2 g, 11.2 mmol) was added polyphosphoric acid (PPA) as a syrup. This was heated at 90° C. with stirring. The solid slowly went into solution (with color change). After approx. 1.5 h, the reaction was quenched with water while stirring, basified to pH 8 and stirred with methylene chloride. The layers were separated and the aqueous layer extracted with methylene chloride (3×100 mL). The combined organic layers were washed with brine, dried (MgSO$_4$), filtered and concentrated to yield an oil which solidified upon standing (1.65 g, 92%). This material was chromatographed to separate the two isomers using 200 g silica gel eluting with hexane/ethyl acetate 9:1 to yield first 6,7-di-methyl-1-indanone as a white solid (740 mg): mp 43°–44° C.; followed by 5,6,-di-methyl-1-indanone as a white solid (925 mg): mp 86.7° C.

Preparation 24. 4,5-di-methyl-2-oximino-1-indanone (A-1, Chart A)

This compound was prepared using the method described in Preparation 1 using 6,7-di-methyl-1-indanone (Preparation 23) to yield the title compound as an off-yellow solid (450 mg, 60%): mp 219°–220° C.

Preparation 25. 5,6-di-methyl-2-oximino-1-indanone (A-1, Chart A)

This compound was prepared using the method described in Preparation 1 using 5,6-di-methyl-1-indanone (Preparation 23) to yield the title compound as an off-white solid (760 mg, 77%): mp 127° C. dec Preparation 26. 4,5-di-methyl-2-aminoindan (A-2, Chart A)

This compound was prepared using the method described in Preparation 4 using 6,7-di-methyl-2-oximino-1-indanone (Preparation 24) to yield the title compound which was used without further purification in Example 38.

Preparation 27. 5,6-di-methyl-2-aminoindan (A-2, Chart A)

This compound was prepared using the method described in Preparation 4 using 5,6-di-methyl-2-oximino-1-indanone (Preparation 25) to yield the title compound which was used without further purification in Example 39.

Preparation 28. 4-(methylphenyl)propionic acid (E-2, Chart E)

The title compound was prepared following the same procedure outlined in Preparation 22 using 4-methyl cinnamic acid (commercially available from Aldrich) to yield a white solid (10.38 g, 100%): mp 115°–116° C.

Preparation 29. 6-methyl-1-indanone (E-3, Chart E)

The title compound was prepared following the same procedure outlined in Preparation 23 using 4-(methylphenyl)propionic acid (Preparation 28) to yield yellowish solid (1.73 g, 99%) as a mixture of product and over-reacted dimer (80:20): $^1$H NMR (CDCl$_3$) δ 7.65–7.22 (m, 3H), 3.11–3.07 (m, 2H), 2.70–2.66 (m, 2H), 2.40 (s, 3H). Material was used without further purification.

Preparation 30. 6-methyl-2-oximino-1-indanone (A-1, Chart A)

The title compound was prepared following the same procedure outlined in Preparation 1, using 6-methyl-1-indanone (Preparation 29) to yield a green solid (0.47 g, 40%): $^1$H NMR (CDCl$_3$) δ 7.67–7.40 (m, 3H), 3.78 (s, 2H), 2.42 (s, 3H); MS theory for C$_{10}$H$_9$O$_2$: 175.0633, observed: 175.0635.

Preparation 31. 6-methyl-2-aminoindan (A-2, Chart A)

The title compound was prepared following the same procedure outlined in Preparation 4, using 6-methyl-2-oximino-1-indanone (Preparation 30) to yield a liquid which was used without purification in Example 40.

Preparation 32. 2-(fluorophenyl)propionic acid (E-2, Chart E)

The title compound was prepared following the same procedure outlined in Preparation 22 using 2-fluoro-cinnamic acid (commercially available from Aldrich) to yield a white solid (3.16 g, 100%): mp 76°–77° C.

Preparation 33. 4-Fluoro-1-indanone (E-3, Chart E)

The title compound was prepared following the same procedure outlined in Preparation 23 using 2-(fluorophenyl) propionic acid (Preparation 32) to yield yellowish solid (590 mg, 66%) as a mixture of product and over-reacted dimer: $^1$H NMR (CDCl$_3$) δ 7.61–7.20(m, 3H), 3.11–3.07 (m, 2H), 2.69–2.65 (m, 2H). Material was used without further purification.

Preparation 34. 4-Fluoro-2-oximino-1-indanone (A-1, Chart A)

The title compound was prepared following the same procedure outlined in Preparation 1, using 4-Fluoro-1-indanone (Preparation 33). No precipitate formed so the reaction mixture was concentrated and ether added. The solid was collected to yield a side product. The mother liquor (540 mg, brown oil) was determined to be the title compound.

Preparation 35. 4-Fluoro-2-aminoindan (A-2, Chart A)

The title compound was prepared following the same procedure outlined in Preparation 4, using 4-Fluoro-2-oximino-1-indanone (Preparation 34) to yield a liquid residue which was used without purification in Example 41.

Preparation 36. 4-(i-propyl)cinnamic acid (E-1, Chart E).

The title compound was prepared following the same procedure outlined in Preparation 21 using 4-(i-propyl)-benzaldehyde (commercially available from Aldrich) to yield a white solid (5.98 g, 93%): mp 157°–159° C.

Preparation 37. 4-(i-propylphenyl)propionic acid (E-2, Chart E)

The title compound was prepared following the same procedure outlined in Preparation 22 using 4-(i-propyl) cinnamic acid (Preparation 36) to yield a white solid (1.95 g, 96%): mp 69°–71° C.

Preparation 38. 6-(i-propyl)-1-indanone (E-3, Chart E)

The title compound was prepared following the same procedure outlined in Preparation 23 using 4-(i-propylphenyl)propionic acid (Preparation 37) to yield an oil (970 mg, 86%): $^1$H NMR (CDCl$_3$) δ 7.64–7.13 (m, 3H), 3.12–3.09 (m, 1H), 2.99–2.87 (m, 2H), 2.72–2.66 (m, 2H), 1.35–1.22 (m, 6H).

Preparation 39. 6-(i-propyl)-2-oximino-1-indanone (A-1, Chart A)

The title compound was prepared following the same procedure outlined in Preparation 1, using 6-(i-propyl)-1- indanone (Preparation 38). No precipitate formed so the reaction mixture was concentrated and ether added. The solid was collected to yield the title compound: mp 188°–190° C.

Preparation 40. 5-(i-propyl)-2-aminoindan (A-2, Chart A)

The title compound was prepared following the same procedure outlined in Preparation 4, using 6-(i-propyl)-2-oximino-1-indanone (Preparation 39) to yield a liquid residue which was used without purification in Example 42

Preparation 41. 2,4-dimethyl-cinnamic acid (E-1, Chart E)

The title compound was prepared following the same procedure outlined in Preparation 21 using 2,4-dimethylbenzaldehyde (commercially available from Aldrich) to yield a white solid (2.92 g, 75%): mp 176°–177° C.

Preparation 42. 2,4-(di-methylphenyl)propionic acid (E-2, Chart E)

The title compound was prepared following the same procedure outlined in Preparation 22 using 2,4-dimethyl-cinnamic acid (Preparation 41) to yield a white solid (1.05 g, 96%): mp 104°–105° C.

Preparation 43. 4,6-dimethyl-1-indanone (E-3, Chart E)

The title compound was prepared following the same procedure outlined in Preparation 23 using 2,4-(di-methylphenyl)propionic acid (Preparation 42) to yield an off-white solid (780 mg, 87%): mp 113–114 C.

Preparation 44. 4,6-dimethyl-2-oximino-1-indanone (A-1, Chart A)

The title compound was prepared following the same procedure outlined in Preparation 1, using 4,6-methyl-1-indanone (Preparation 43). No precipitate formed so the reaction mixture was concentrated and ether added. The solid was collected to yield the title compound as a yellow solid (565 mg, 70%); mp>200° C. dec.

Preparation 45. 4,6-dimethyl-2-aminoindan (A-2, Chart A)

The title compound was prepared following the same procedure outlined in Preparation 4, using 4,6-dimethyl-2-oximino-1-indanone (Preparation 44) to yield a liquid residue which was used without purification in Example 44

Preparation 46. 2,5-dimethyl-cinnamic acid (E-1, Chart E)

The title compound was prepared following the same procedure outlined in Preparation 21 using 2,5-dimethylbenzaldehyde (commercially available from Aldrich) to yield a white solid (3.19 g, 82%): mp 129°–131° C.

Preparation 47. 2,5-(di-methylphenyl)propionic acid (E-2, Chart E)

The title compound was prepared following the same procedure outlined in Preparation 22 using 2,5-dimethyl-cinnamic acid (Preparation 46) to yield a clear oil (0.95 g, 94%): $^1$H NMR (CDCl$_3$) δ 7.05–6.93 (m, 3H), 2.94–2.89 (m, 2H), 2.65–2.60 (m, 2H), 2.29 (s, 3H), 2.28 (s, 3H).

Preparation 48. 4,7-dimethyl-1-indanone (E-3, Chart E)

The title compound was prepared following the same procedure outlined in Preparation 23 using 2,5-(di-methylphenyl)propionic acid (Preparation 47) to yield an off-white solid (678 mg, 79%): mp 65°–72° C.

Preparation 49. 4,7-dimethyl-2-oximino-1-indanone (A-1, Chart A)

The title compound was prepared following the same procedure outlined in Preparation 1, using 4,7-methyl-1-indanone (Preparation 48). No precipitate formed so the reaction mixture was concentrated and ether added. The solid was collected to yield the title compound (650 mg, 41%): mp 209°–210° C.

Preparation 50. 4,7-dimethyl-2-aminoindan (A-2, Chart A)

The title compound was prepared following the same procedure outlined in Preparation 4, using 4,7-dimethyl-2-oximino-1-indanone (Preparation 49) to yield a liquid residue which was used without purification in Example 45.

Preparation 51. 4-propyl-cinnamic acid (E-1, Chart E).

The title compound was prepared following the same procedure outlined in Preparation 21 using 4-propyl-benzaldehyde (commercially available from Kodak) to yield a white solid (3.75 g, 97%): mp 158°–160° C.

Preparation 52. 4-(propylphenyl)propionic acid (E-2, Chart E)

The title compound was prepared following the same procedure outlined in Preparation 22 using 4-propyl-cinnamic acid (Preparation 51) to yield a white solid (1.99 g, 99%): mp 66°–70° C.

Preparation 53. 6-propyl-1-indanone (E-3, Chart E)

The title compound was prepared following the same procedure outlined in Preparation 23 using 4-(propylphenyl) propionic acid (Preparation 52) to yield an oil (780 mg, 88%): $^1$H NMR (CDCl$_3$) δ 7.66–7.11 (m, 3H), 3.12–3.09 (m, 1H), 2.71–2.52 (m, 4H), 1.74–1.58 (m, 2H), 1.5–0.98 (m, 3H).

Preparation 54. 6-propyl-2-oximino-1-indanone (A-1, Chart A)

The title compound was prepared following the same procedure outlined in Preparation 1, using 6-propyl-1-indanone (Preparation 53). No precipitate formed so the reaction mixture was concentrated and used without further purification: MS m/e 203, 186, 174, 160, 146, 129, 116; HR MS theory for $C_{12}H_{13}NO_2$: 203.0946, observed: 203.0960.

Preparation 55. 5-propyl-2-aminoindan (A-2, Chart A)

The title compound was prepared following the same procedure outlined in Preparation 4, using 6-propyl-2-oximino-1-indanone (Preparation 54) to yield a liquid residue which was used without purification in Example 46

Preparation 56. 4-(t-butylphenyl)propionic acid (E-2, Chart E)

The title compound was prepared following the same procedure outlined in Preparation 22 using 4-(t-butyl)-cinnamic acid (commercially available form EMKA-Chemie) to yield a white solid (1.96 g, 97%): mp 111°–112° C.

Preparation 57. 6-(t-butyl)-1-indanone (E-3, Chart E)

The title compound was prepared following the same procedure outlined in Preparation 23 using 4-(t-butyl)-phenyl)propionic acid (Preparation 56) to yield an yellow solid (900 mg, 56%): $^1$H NMR (CDCl$_3$) δ 7.78 (d, J=1.8 hz, 1H), 7.68–7.65 (dd, J=1.9 Hz, 8.0 Hz, 1H), 7.43–7.41 (d, J=8 Hz, 1H), 3.12–3.08 (m, 2H), 2.72–2.68 (m, 2H), 1.34 (s, 9H).

Preparation 58. 6-(t-butyl)-2-oximino-1-indanone (A-1, Chart A)

The title compound was prepared following the same procedure outlined in Preparation 1, using 6-(t-butyl)-1-indanone (Preparation 57) to yield a white solid: mp 220°–221° C.

Preparation 59. 5-(t-butyl)-2-ammoindan (A-2, Chart A)

The title compound was prepared following the same procedure outlined in Preparation 4, using 6-(t-butyl)-2-oximino-1-indanone (Preparation 54) to yield a liquid residue which was used without purification in Example 47

EXAMPLE 1

5-Fluoro-2-(di-n-propylamino)indan (A-3, Chart A).

The title compound was prepared from 5-fluoro-2-aminoindan (Preparation 6) using the preparation outlined in Preparation 7 to yield a white solid; mp 160°–161° C.

EXAMPLE 2

5-(trifluoromethylsulfonyloxy)-2-(n-propylamino)indan (A-4 Chart A).

To a solution of 5-hydroxy-2-(n-propylamino)indan (Preparation 9, free base, 150 mg, 0.5 mmol), 2,6 lutidine (0.15 mL), 2 mg dimethylaminopyridine in methylene chloride (20 mL) at −30° C. was added triflic anhydride (0.13 mL, 9.75 mmol). The solution was allowed to warm to room temperature. The reaction was extracted with methylene chloride and 10% HCl. The organic layers were washed with brine, dried, filtered, and concentrated to yield an oil. The oil was chromatographed on 400 mg silica gel eluting with methylene chloride/methanol (19:1) to yield an oil. The HCl salt was made and recrystallized from methanol/ethyl acetate to yield a white solid; mp 188°–194° C.

EXAMPLE 3

5,6-(di-trifluoromethylsulfonyloxy)-2-(n-propylamino) indan (A-4, Chart A).

The title compound was synthesized using the procedure outlined in Example 6 using 5,6-dihydroxy-2-(n-propylamino)indan (Preparation 10) and was recrystallized from ether/ethyl acetate to yield a white solid (129 mg, 90%); mp 157°–163° C.

EXAMPLE 4

5,6-Methylenedioxy-2-(di-n-propylamino)indan (B-1, Chart B).

5,6-Dihydroxy-2-(di-n-propylamino)indan hydrobromide (400 mg, 1.21 mmol) was dissolved in dimethylformamide/acetonitrile (8 mL, 1:1). Potassium carbonate (1.67 g, 12.1 mmol) and 1,2-dibromomethane (0.09 mL, 1.3 mmol) was added and the mixture was heated at 100° C. overnight. Water was added and the reaction mixture concentrated to remove solvents. The resulting mixture was extracted with ethyl acetate (5×75 mL). The combined organic layers were washed with brine, dried, filtered and concentrated to yield an oil. The crude material was chromatographed (200 g silica gel) eluting with methylene chloride/methanol (19:1) to yield an oil. The oil was converted into the HCl salt and recrystallized using methanol/ethyl acetate/ether: mp 168°–269° C.

EXAMPLE 5

5,6-Ethylenedioxy-2-(di-n-propylamino)indan (B-1, Chart B).

5,6-Dihydroxy-2-(di-n-propylamino)indan hydrobromide (200 mg, 0.6 mmol) was reacted with 1,2-dibromoethane (0.05 mL, 0.66 mmol) under the same reaction conditions as Example 4. The crude material was chromatographed (200 g silica gel) eluting with methylene chloride/methanol (9:1) to yield an oil. The oil was converted into the HCl salt and recrystallized using methanol/ethyl acetate/ether: mp 210°–215° C.

EXAMPLE 6

5,6-dimethoxy-2(pyrrolidino)indan (A-3, Chart A).

To a solution of 5,6-dimethoxy-2-aminoindan (Preparation 5, 4.5 mmol) in dimethylformamide/acetonitrile (1:6, 49 mL) was added sodium carbonate (1.43 g, 13.5 mmol) and was heated (100° C.) overnight. The mixture was diluted with ethyl acetate, filtered and the filtrate concentrated. The oily residue was chromatographed (400 g silica gel) eluting with methylene chloride/methanol (9:1) to yield a yellow oil. The oil was converted into the HCl salt and recrystallized from methanol/ethyl acetate: mp 267°–269° C.

EXAMPLE 7

5-(trifluoromethylsulfonyloxy)-6-hydroxy-2-(di-N-propylamino)indan (A-6, Chart A).

A mixture of 5,6-(di-trifluoromethylsulfonyloxy)-2-(di-N-propylamino)indan (Example 3, 4 mmol) and triethylamine (4.4 mmol, 0.6 mL) in DMF/methanol (3:1, 20 mL) was heated at 70° C. for 3 h. The reaction was quenched with water and extracted with methylene chloride. The combined organic layers were washed with water, brine, dried ($MgSO_4$), filtered and concentrated to give a dark brown oil. Chromatography using 400 g, silica, eluting with hexane/acetone (3:1) yielded a light yellow oil (1.18 g, 78%). The HCl salt was formed and crystallized from ethyl acetate/methanol to give the title compound as a white solid; mp 235°–237° C.

EXAMPLE 8

5-(trifluoromethylsulfonyloxy)-6-acetoxy-2-(di-N-propylamino)indan (A-5, Chart A).

5-(trifluoromethylsulfonyloxy)-6-hydroxy-2-(di-N-propylamino)indan (Example 7, 1.18 g, 3.1 mmol) was stirred in a mixture of acetic anhydride (1 mL), pyridine (2 mL) and methylene chloride (10 mL) at rt for 24 h. The reaction was quenched with methanol (2 mL), stirred for 1 h followed by extraction using methylene choride. The organic layers were washed with water, satd. sodium bicarbonate, brine, dried ($MgSO_4$), filtered and concentrated. The oil was chromatographed on 400 mg silica gel eluting with hexane/acetone (3:1) to geive a light yellow oil. The HCl salt was formed and crystallized from methanol/ethyl acetate/hexane to yield the title compound as a white solid: mp 190°–191° C.

EXAMPLES 9 AND 10

5,6-(di-carbomethoxy)-2-(di-N-propylamino)indan (A-5, Chart A) and 5-(carbomethoxy)-6-hydroxy-2-(di-N-propylamino)indan (A-6, Chart A)

To a solution of 5,6-(di-trifluoromethylsulfonyloxy)-2-(di-N-propylamino)indan (Example 3, 15 mmol, 7.7 g) and triethylamine (66 mmol) in methanol/DMF (1:3) which had been degassed with nitrogen followed by CO (gas) was added a solution of palladium acetate (3 mmol) and dppp (1,3-bis(diphenylphosphino)-propane) in DMF/methanol (3:1) which had also been degassed with nitrogen. The bubbling of CO gas continued for 6 hours at 60° C. The mixture was cooled to rt, acidified with 6N HCl and basified with saturated sodium bicarbonate. This mixture was extracted with ethyl acetate/hexane (3:1, 2×800 mL). The organic layer was washed with water, brine, dried ($MgSO_4$), filtered and concentrated to give a brown oil. The oil was chromatographed on 800 g silica gel eluting with hexane/acetone (3:1) to give 5-(carbomethoxy)-6-hydroxy-2-(di-N-propylamino)indan as the leasst polar product (0.37 g). This was converted to the HCl salt and crystallized from ethyl acetate/methanol to give white solid: mp 178°–179° C. Also, 5,6-(di-carbomethoxy)-2-(di-N-propylamino)indan was obtained (0.4 g). The HCl salt was formed and crystallized from ethyl acetate/methanol to give a white solid: mp 202°–203° C. The major product was 5-(trifluoromethylsulfonyloxy)-6-hydroxy-2-(di-N-propylamino)indan (3.3 g) (see Example 7).

EXAMPLE 11

5-Bromo-2-(dipropylamino)indan. (C-2, Chart C)

Lithium aluminium hydride (90 mg, 2.36 mmol) and aluminium chloride (350 mg, 2.25 mmol) were added to dry THF (25 mL). The mixture was cooled to −15° C. and kept at this temperature for 15 min. N-(6-Bromo-indan-2-yl)-N-propyl-propionamide (preparation 14, 0.35 g, 1.13 mmol) dissolved in dry THF (10 mL) was added and the reaction mixture was stirred at −15° C. for 90 min. Aqueous NaOH (15 mL, 15%) was added and the mixture extracted with ethyl acetate. The layers were separated and the organic layer washed with water, dried ($Na_2CO_3$) and the solvent was evaporated to dryness. The crude product was chromatographed and the pure fractions were pooled, yielding 280 mg (83%) of (6-bromo-indan-2-yl)-dipropyl-amine as the free base. The amine was converted to its hydrochloride salt with EtOH-HCl and recrystallized from a mixture of 2-propanol and isopropyl ether. m.p. 196°–198° C. (HCl); $^1H$ NMR (300 MHz, $CDCl_3$) δ 0.90 (t, 6H), 1.50 (m, 4H), 2.50 (t, 4H), 2.75–3.08 (m, 4H), 3.60–3.75 (p, 1H), 7.05 (d, J=8 Hz, 1H), 7.28 (d, J=8 Hz, 1H), 7.32 (s, 1H); $^{13}C$ NMR (75.4 MHz, $CDCl_3$) δ 12.02, 20.30, 36.25, 36.62, 53.39, 63.25, 119.82, 125.95, 127.56, 129.26, 141.00, 144.47; MS m/e 295 (6, M+), 269 (100), 266 (98), 116 (54), 115 (41).

EXAMPLE 12

(6-Methylsulfanyl-indan-2-yl)-dipropyl-amine. (C-2, Chart C)

Distilled (6-bromo-indan-2-yl)-dipropyl-amine (Example 11, 270 mg, 0.91 mmol) was dissolved in dry diethyl ether (20 mL). The solution was kept under argon and cooled to −78° C. A solution of t-BuLi in pentane 1.7M (0.7 mL, 1.20 mmol) was added and the mixture was stired at −78° C. for 1 h. Freshly distilled methyl disulfide (0.14 mL, 1.55 mmol) was added at −78° C. and the mixture was stirred at this temperature for 30 min. The reaction mixture was allowed to reach room temperature and stirred for an additional 1 h. The organic layer was washed with aq. $Na_2CO_3$ (5%), the layers separated, dried ($Na_2CO_3$) and evaporated to dryness. The crude product was chromatograped ($SiO_2$) using dichloromethane-methanol (45:1) as eluant. The pure fractions were pooled yielding 180 mg (75%) of (6-methylsulfanyl-indan-2-yl)-dipropyl-amine. The free base was converted to the hydrochloride salt and recrystallized from a mixture of 2-propanol and isopropyl ether. m.p. 180–182 (HCl); $^1H$ NMR (300 MHz, $CDCl_3$) δ 0.90 (t, 6H), 1.55 (m, 4H), 2.45–2.60 (m, 7H), 2.80–3.10 (m, 4H), 3.60–3.75. m (1), 7.05–7.20 (m, 3H); $^{13}C$ NMR (75.4 MHz, $CDCl_3$) δ 12.01, 16.67, 20.21, 36.22, 36.64, 59.43, 63.32, 123.39, 124.81, 125.49, 135.70, 139.38, 142.91; MS m/e 263 (12, M+), 235 (100), 163 (31), 115 (23), 116 (17).

EXAMPLE 13

(6-Methylsulfonyl-indan-2-yl)-dipropyl-amine. (C-2, Chart C)

To a solution of (6-methylsulfanyl-indan-2-yl)-dipropyl-amine (Example 12, 85 mg, 0.32 mmol) in trifluoromethane-sulfonic acid (5 ml) was added 3-chloroperoxy-benzoic acid (90 mg, 75%, 0.39 mmol). The solution was then stirred for 2 h at room temperature. Another portion of 3-chloroperoxy-benzoic acid (20 mg 75%, 0.09 mmol) was added and the reaction mixture was stirred for an additional 1 h. The pH was adjusted to 11 with aqueous $Na_2CO_3$ and the layers were separated. The organic layer was dried and evaporated to dryness. The crude product was chromatographed ($SiO_2$) using dichloromethane-methanol as eluant (19:1). Pooling of the pure fractions yielded 65 mg (69%) of (6-methylsulfonyl-indan-2-yl)-dipropyl-amine. The amine was converted to the hydrochloride and recrystallized from a mixture of 2-propanol and isopropyl ether. m.p. 190–192 (HCl); $^1H$ NMR (300 MHz, $CDCl_3$) δ 0.90 (t, 6H), 1.50 (m, 4H), 2.50 (t, 4H), 2.90–3.20 (m, 7H), 3.70–3.80 (m, 1H), 7.40 (d, J=8 Hz, 1H), 7.70–7.80 (d, 2H); $^{13}C$ NMR (75.4 MHz, $CDCl_3$) δ 11.97, 20.25, 36.43, 36.82, 44.68, 53.29, 63.08, 123.33, 125.18, 125.81, 138.65, 143.72, 148.89; MS m/e 295 (5, M+), 266 (100), 116 (18), 267 (18), 115 (15).

EXAMPLE 14

(6-Methylsulfinyl-indan-2-yl)-dipropyl-amine. (C-2, Chart C)

From the chromatographic separation of the of crude (6-methylsulfonyl-indan-2-yl)-dipropyl-amine (Example 13), 5 mg (6%) (6-Methylsulfinyl-indan-2-yl)-dipropyl-amine was isolated. The amine was converted to its hydrochloride salt and recrystallized from a mixture of 2-propanol and isopropyl ether. m.p. 148°–152° C. (HCl); $^1H$ NMR (300 MHz, $CDCl_3$) δ 0.90 (t, 6H), 1.50 (m, 4H), 2.50 (t, 4H), 2.70 (s, 3H), 2.90–3.20 (m, 4H), 3.65–3.80 (m, 1H), 7.30 (d, J=8 Hz, 1H), 7.40 (d, J=8 Hz, 1H), 7.50 (s, 1H); $^{13}C$ NMR (75.4 MHz, $CDCl_3$) δ 11.96, 20.10, 36.47, 36.55, 44.08, 44.12, 53.30, 63.17, 63.24, 119.49, 121.90, 121.94, 125.21, 143.62, 145.73; MS m/e 279 (7, M+), 250 (100), 234 (96), 235 (69), 163 (33), 115 (33).

EXAMPLE 15

2-Dipropylamino-indan-5-carbaldehyde. (C-2, Chart C)

Distilled (6-bromo-indan-2-yl)-dipropyl-amine (Example 11, 270 mg, 0.91 mmol) was dissolved in dry diethyl ether (20 mL). The solution was kept under argon and cooled to −78° C. A solution of t-BuLi in pentane 1.7M (0.7 mL, 1.20 mmol) was added and the mixture was stired at −78° C. for 1 h. Freshly distilled DMF (0.12 mL, 1.55 mmol) was added at −78° C. and the mixture was stirred at this temperature for 30 min. The reaction mixture was allowed to reach room temperature and stirred for additional 1 h. The organic layer was washed with aq. $Na_2CO_3$ (5%), the layers separated, dried ($Na_2CO_3$) and evaporated to dryness. MS m/e 245 (11, M+), 216 (100), 145 (17), 117 (22), 72 (21).

EXAMPLE 16

(5-Iodo-indan-2-yl)-dipropyl-amine and (4-Iodo-indan-2-yl)-dipropyl-amine. (C-2, Chart C)

To a solution of N-(5-Iodo-indan-2-yl)-N-propyl-propionamides and N-(4-Iodo-indan-2-yl)-N-propyl-propionamides (0.3 g, ratio 96:4, prepation 15), dissolved in a mixture of dichloromethane/1,2-dichloroethane (30 ml, 1:1) was added $QBH_4$ (0.7 g). The reaction mixture was refluxed overnight. The solvents were removed by evaporation and the residue was refluxed for 1 h in a 10% hydrochloride solution. The resulting aqueous phase was extracted with EtOAc, basified with 10% $Na_2CO_3$ and extracted with dichloromethane. The combined organic phases were dried ($MgSO_4$), filtered and evaporated to dryness yielding a mixture of two regioisomers with similar mass spectra: MS m/e 343 (7, M+), 314 (100), 243 (22), 188 (11), 116 (29), 72 (15).

EXAMPLE 17

Toluene-4-sulfonic acid 2-dipropylamino-indan-5-yl ester. (A-4, Chart A)

2-Dipropylamino-indan-5-ol (Preparation 9, 140 mg, 0.47 mmol) was dissolved in dichloromethane (25 mL) and cooled to 0 C. Thereafter was added triethylamine (99 mg, 0.98 mmol) and toluene-4-sulfonyl chloride (101 mg, 0.54 mmol). The reaction mixture was allowed to reach room temperature and was then stirred at ambient temperature for 2 h. Aqueous $Na_2CO_3$ solution (25 mL, 10%) was added and the mixture was stirred for an additional 5 min. The layers were separated and the organic layer was washed, dried ($Na_2SO_4$) and the solvent evaporated. The crude product was chromatograped using dichloromethane-methanol (19:1) as eluant. The pure fractions were pooled, and the solvent removed in vacuo yielding 135 mg (78%) of toluene-4-sulfonic acid 2-dipropylamino-indan-5-yl ester as an oil. The amine was converted to its hydrochloride salt (hydroscopic).; $^1H$ NMR (300 MHz, $CDCl_3$) δ 0.85 (t, 6H), 1.45 (m, 4H), 2.4–2.5 (m, 7H), 2.75–2.85 (m, 2H), 2.90–3.00 (m, 2H), 3.60–3.70 (m, 1H), 6.65 (dd, J=2.5, 8.3 Hz, 1H), 6.85 (d, J=2.5 Hz, 1H), 7.05 (d, J=8.0 Hz, 1H), 7.30 (d, J=8.5 Hz, 2H), 7.70 (d, J=8.7 Hz, 2H); $^{13}C$ NMR (75.4 MHz, $CDCl_3$) δ 11.99, 20.24, 21.73, 36.11, 36.70, 53.37, 63.44, 118.57, 120.14, 125.03, 128.51, 129.67, 132.60, 140.96, 143.74, 145.16, 148.27; MS m/e 387 (3, M+), 358 (100), 232 (49), 91 (15), 155 (13).

EXAMPLE 18

Toluene-4-sulfonic acid 2-dipropylamino-6-hydroxy-indan-5-yl ester. (A-5, Chart A)

To a solution of 5,6-ditosylate-indan-2 yl)-dipropylamine (90 mg, 0.16 mmol) in acetone (20 ml) was added aq. sodium hydroxide (15%, 20 ml). The mixture was then refluxed over night. Thin layer chromathography at this time, indicated complete conversion of the starting material (dichloromethane:methanol 19:1). The solution was acidified by the addition of aq., hydrochloric acid (10%) and then extracted with dichloromethane. The combined organic phases were dried ($MgSO_4$), filtered and evaporated to dryness. The crystalline residue material was recrystallized from 2-propanol/di-isopropyl ether (45 mg, 63%): m.p. 225°–230° C. (HCl); $^1H$ NMR (300 MHz, $CDCl_3$) δ 0.90 (t, 6H), 1.50 (m, 4H), 2.50 (m, 7H), 2.70–3.0 (m, 4H), 3.65 (m, 1H), 4.3 (s, br, 1H), 6.67 (s, 1H), 6.77 (s, 1H), 7.32 (d, J=8 Hz, 1H), 7.76 (d, J=8 Hz, 1H); $^{13}C$ NMR (75.4 MHz, $CD_3OD$, HCl salt) d 12.8, 20.1, 23.2, 36.7, 37.3, 55.6, 66.7, 115.6, 122.2, 131.4, 132.2, 135.7, 139.9, 141.4, 148.5, 152.2.

EXAMPLE 19

(2-Dipropylamino-indan-5-yl)-phenyl-methanone and (2-Dipropylamino-indan-4-yl)-phenyl-methanone. (A-3, Chart A)

To a solution of 2-dipropylamino-indan (100 mg, 0.46 mmol) in nitrobenzene (30 mL) was added aluminumchloride (0.3 g, 2.3 mmol). The reaction was stirred for 1 h at 4° C. followed by benzoylchloride in one portion (0.165 ml, 1.84 mmol). After 24 h the solution was evaporated and redissolved in dichloromethane (30 ml). Aqueous Na2CO3 solution (40 ml; 10%) was added and the mixture stirred for 30 min. The organic layer was separated, washed with water, dried (Na2SO4) and evaporated. The crude product was chromatographed using dichloromethane:methanol (24:1) as eluant. The pure fractions were pooled, yielding 11 mg (8%) of two regioisomers (10:1). These showed similar mass spectra: (MS m/e 321 (4, M+), 293 (23), 292 (100), 105 (35), 77 (14).

EXAMPLE 20

N-[2-(Benzyl-propyl-amino)-indan-5-yl]-4-methyl-benzene-sulfonamide. (D-1, Chart D)

To a stirred solution of N-2-benzyl-N-2-propyl-indan-2, 6-diamine (133 mg, 0.47 mmol) (from, PCT/US94/02800) in dichloromethane (5 ml) was added toluene sulfonyl chloride (100 mg, 0.52 mmol) followed by addition of triethylamine (70 μL, 0.51 mmol). The mixture was stirred at ambient temperature for 2 hrs. and then the mixture was quenched by the addition of saturated sodium carbonate solution (5 mL). The organic layer was separated and the aqueous layer was extracted with dichloromethane. The combined organic phases were dried over magnesium sulfate and the solvent removed to yield 217 mg of the crude product. This material was then purified by column chromatography ($SiO_2$), eluting with n-hexane-ethyl acetate 6:1. Concentration of the collected fractions yielded 205 mg (90%) as a colorless oil.: $^1H$ NMR (300 MHz, $CDCl_3$) δ 0.88 (t, 3H), 1.50 (m, 2H), 1.6 (sb, 1H), 2.48 (s, 3H), 2.50 (m, 2H), 2.96 (m, 4H), 3.63 (s, 2H), 3.80 (m, 1H), 6.72 (dd, 1H), 6.82 (s, 1H), 7.12 (d, 1H), 7.2–7.4 (m, 7H), 7.81 (m, 2H); $^{13}C$ NMR (75.4 MHz, $CDCl_3$) δ 11.90, 20.22, 21.72, 35.62, 35.80, 53.05, 55.52, 62.47, 124.94, 126.73, 127.42, 128.20, 128.49, 128.61, 129.50, 132.36, 136.63, 136.82, 140.49, 143.35, 144.70, 144.86; MS (EI) m/e 434 (6, M+), 91 (100), 279 (93), 207 (57), 250 (41), 130 (17).

EXAMPLE 21

N-[2-(Benzyl-propyl-amino)-indan-5-yl]-methanesulfonamide. (D-1, Chart D)

To a stirred solution of N-2-benzyl-N-2-propyl-indan-2, 6-diamine (133 mg, 0.47 mmol) (from, PCT/US94/02800) in dichloromethane (5 ml) was added methanesulfonyl chloride (40 μL, 0.51 mmol) followed by addition of triehylamine (70 μL, 0.51 mmol). The mixture was stirred at ambient temperature for 1 h and then the mixture was quenched by the addition of saturated sodium carbonate solution (5 mL). The organic layer was separated and the aqueous layer was extracted with dichloromethane. The combined organic phases were dried over magnesium sulfate and the solvent removed to yield 180 mg of the crude product. This material was then purified by column chromatography ($SiO_2$), eluting with iso-octane-ethyl acetate 3:1. Concentration of the collected fractions yielded 160 mg (96%) as a colorless oil.: $^1H$ NMR (300 MHz, $CDCl_3$) d 0.88 (m, 3H), 1.50 (m, 2H), 2.48 (m, 2H), 2.99 (m, 4H), 3.37 (s, 3H), 3.67 (s, 2H), 3.80 (m, 1H), 7.1–7.4 (m, 8H); $^{13}C$ NMR (75.4 MHz, $CDCl_3$) δ 11.89, 20.19, (25.71, 30.11), (35.60, 42.58), (35.75, 42.70), 53.06, 55.58, 62.59, 125.55, 126.60, 126.78, 128.20, 128.51, 131.45, 140.33, 144.05, 145.20; Dual signals due to rotameric forms of the sulfonamide group indicated by parentheses; MS (EI) m/e 358 (7, m+), 329 (100), 91 (64), 279 (37), 250 (15), 130 (12), 210 (9), 188 (8).

EXAMPLE 22

2-[2-(Benzyl-propyl-amino)-indan-5-yl]-isoindole-1,3-dione. (D-1, Chart D)

To a stirred solution of N-2-benzyl-N-2-propyl-indan-2, 6-diamine (160 mg, 0.57 mmol) (from, PCT/US94/02800) in acetic acid (5 ml) was added phtalic anhydride (93 mg, 63 mmol). The mixture was heated at reflux for 1 h. After cooling, the solvent was removed in vacuo. The residue was taken up in diethyl ether, washed with saturated sodium carbonate solution and dried over anhydrous sodium carbonate. Removal of the solvent yielded 206 mg (88%) of the pure product as an yellowish oil: $^1$H NMR (300 MHz, CDCl$_3$) δ 0.87 (t, 3H), 1.51 (m, 2H), 2.49 (m, 2H), 3.05 (m, 4H), 3.67 (s, 2H), 3.82 (m, 1H), 7.1–7.5 (m, 8H), 7.75 (m, 2H), 7.95 (m, 2H); $^{13}$C NMR (75.4 MHz, CDCl$_3$) δ 11.92, 20.17, 35.73, 35.94, 53.00, 55.53, 62.46, 122.97, 123.70, 124.93, 125.05, 126.70, 128.17, 128.57, 129.66, 131.85, 134.31, 140.49, 142.55, 143.27, 167.57; MS (EI) m/e 410 (6, M+), 381 (100), 91 (47), 262 (23), 352 (12), 115 (12), 130 (10), 289 (10), 250 (10).

EXAMPLE 23

Benzyl-propyl-(6-pyrrol-1-yl-indan-2-yl)-amine. (D-1, Chart D)

A solution of N-2-benzyl-N-2-propyl-indan-2,6-diamine (114 mg, 0.41 mmol) (from, PCT/US94/02800) and 2,5-dimethoxy-tetrahydrofuran (56 μL, 56 mg, 0.42 mmol) was heated at 100° C. for 2 hrs. The mixture was concentrated in vacuo and then slurried in 2M NaOH. Extraction using diethyl ether yielded 115 mg (85%) of the desired material as an oil.: $^1$H NMR (300 MHz, CDCl$_3$) δ 0.80 (t, 3H), 1.42 (na, 2H), 2.40 (t, 2H), 2.91 (m, 4H), 3.58 (s, 2H), 3.71 (m, 1H), 6.22 (s, 2H), 6.93 (s, 2H), 7.0–7.4 (m, 8H); MS m/e 330 (M+, 15), 301 (100), 91 (35), 182 (6).

EXAMPLE 24

Propyl-(6-pyrrol-1-yl-indan-2-yl)-amine. (D-2, Chart D)

A mixture of benzyl-propyl-(6-pyrrol-1-yl-indan-2-yl)-amine (540 mg, 1.64 mmol), ammonium formate (0.8 g, 12.6 mmol) and 10% Pd/C (0.3 g) in 99% ethanol (50 mL) was stirred for at ambient temperature for 1 h. The mixture was filtered on a Celite pad and the solution concentrated in vacuo. The residue was redissolved in 10% sodium carbonate/diethyl ether. After 2 additional ether extractions of the aqueous phase, the combined ethereal phases were dried (magnesium sulfate) filtered and evaporated to yield 320 mg of a residue containing both the pyrrolo and the pyrrolidino derivative. The two compounds were separated on a silica column using methanol as eluant, yielding 230 mg (58%) of the pyrrolo derivative and 40 mg (10%) of the pyrrolidino derivative.: $^1$H NMR (300 MHz, CDCl$_3$) δ 0.93 (t, 3H), 1.52 (m, 2H), 2.61 (t, 2H), 2.77 (m, 2H), 3.18 (m, 2H), 3.67 (m, 1H), 6.31 (m, 2H), 7.03 (m, 2H), 7.1–7.3 (m, 3H); MS m/e 240 (M+, 72), 211 (100), 182 (72), 171 (65), 115 (25).

EXAMPLE 25

Propyl-(6-pyrrolidin-1-yl-indan-2-yl)-amine. (D-2, Chart D)

The preparation of this material is described in Example 24: MS m/e 244 (M+, 97), 174 (100), 187 (66), 215 (15).

EXAMPLE 26

Dipropyl-(6-pyrrolidin-1-yl-indan-2-yl)-amine. (D-3, Chart D)

To a solution of propyl-(6-pyrrol-1-yl-indan-2-yl)-amine (50 mg, 0.21 mmol) and methylamine (30 μL) in dichloromethane (5 mL) was added propionic acid chloride (20 μL). After stirring at ambient temperature for 1 h was added 10% sodium carbonate. After vigorous stirring for an additional 10 min the phases were separated and the organic phase dried (magnesium sulfate), filtered and evaporated to yield 63 mg (100%) of the propionamide [MS m/e: 296 (M+1), 181 (100), 115 (7)]. This material was dissolved in diethyl ether (5 mL) to which lithium aluminum hydride (35 mg, 0.92 mmol) was added. The slurry was stirred at ambient temperature for 1 h. Water (35 μL) and 15% sodium hydroxide (35 μL) followed by water (105 μL) was added and the mixture was stirred for an additional 10 min. The solid material was filtered off. The ethereal solution was dried (magnesium sulfate), filtered and evaporated to a yield a residue of 50 mg. Chromatographic separation on silica using methanol as eluant yielded 45 mg (76%) of the desired material as an oil.: $^1$H NMR (300 MHz, CDCl$_3$) δ 0.88 (t, 6H), 1.50 (m, 4H), 2.49 (m, 4H), 2.90 (m, 2H), 3.05 (m, 2H), 3.70 (m, 1H), 6.32 (m, 2H), 7.05 (m, 2H), 7.15 (m, 3H); MS m/e 282 (M+, 15), 253 (100), 182 (35), 165 (12).

EXAMPLE 27

N-[2-(benzyl-propyl-amino)-indan-5-yl]acetamide. (D-1, Chart D)

To a solution of N-2-benzyl-N-2-propyl-indane-2,6-diamine (75 mg, 0.27 mmol) (from, PCT/US94/02800) triethylamine (200 μL) in dichloromethane (5 mL) was added acetyl chloride (56 μL, 0.65 mmol). The mixture was stirred for 5 h. Sodium carbonate (10%, 5 mL) was added and the mixture was stirred for additional 30 min. The organic phase was dried (magnesium sulfate), filtered and evaporated to yield 85 mg (100%) of the pure material as an oil.: $^1$H NMR (300 MHz, CDCl$_3$) δ (0.72,1.10) (t, 3H), 1.35 (m, 2H), 2.05 (s, 3H), 2.35 (m, 2H), 2.82 (m, 4H), 3.53 (s, 2H), 3.62 (m, 1H), 6.9–7.4 (m, 8H), 7.55 (sb, 1H) Shift values within parentheses indicate dual signals due to amide rotameric forms.; MS m/e 322 (M+, 11), 293 (100), 91 (40), 264 (18).

EXAMPLE 28

Cyclopropanecarboxylic acid [2-(benzyl-propyl-amino)-indan-5-yl]amide. (D-1, Chart D)

To a solution of N-2-benzyl-N-2-propyl-indan-2,6-diamine (105 mg, 0.38 mmol) (from, PCT/US94/02800) triethylamine (200 μL) in dichloromethane (10 mL) was added cyclopropanecarboxylic acid chloride (43.7 mg, 38 μL, 0.42 mmol). The mixture was stirred over night. Sodium carbonate (10%, 10 mL) was added and the mixture was stirred for additional 30 min. The organic phase was dried (magnesium sulfate), filtered and avaporated to yield 120 mg (91%) of the pure material as an oil.: $^1$H NMR (300 MHz, CDCl$_3$) δ 0.6–1.2 (m, 8H), 1.45 (m, 2H), 2.40 (m, 2H), 2.88 (d, 4H), 3.62 (s, 2H), 3.64 (m, 1H), 6.9–7.4 (m, 8H); MS m/e 348 (M+, 10), 319 (100), 91 (30), 222 (14), 290 (11).

EXAMPLE 29

N-[2-(benzyl-propyl-amino)-indan-5-yl]propionumide. (D-1, Chart D)

To a solution of N-2-benzyl-N-2-propyl-indan-2,6-diamine (93 mg, 0.33 mmol) (from, PCT/US94/02800) and triethylamine (200 μL) in dichloromethane (5 mL) was added propionic acid chloride (33.6 mg, 3 μL, 0.36 mmol). The mixture was stirred for 2 h. Sodium carbonate (10%, 5 mL) was added and the mixture was stirred for additional 30 min. The organic phase was dried (magnesium sulfate), filtered and evaporated to yield 107 mg (96%) of the pure material as an oil.: $^1$H NMR (300 MHz, CDCl$_3$) δ 0.73 (t, 3H), 1.10 (t, 3H), 1.41 (m, 2H), 2.22 (m, 2H), 2.36 (m, 2H), 2.82 (d, 4H), 3.55 (s, 1H), 3.61 (m, 1H), 6.9–7.4 (m, 8H); MS m/e 336 (11), 307 (100), 91 (39), 278 (16), 222 (15).

EXAMPLE 30

N-[2-(benzyl-propyl-amino)-indan-5-yl]-2,2-dimethyl-propionamide. (D-1, Chart D)

To a solution of N-2-benzyl-N-2-propyl-indan-2,6-diamine (111 mg, 0.39 mmol) (from, PCT/US94/02800) and triethylamine (200 µL) in dichloromethane (10 mL) was added di-methyl propionic acid chloride (51.7 mg, 52.7 µL, 0.43 mmol). The mixture was stirred for 5 h. Sodium carbonate (10%, 10 mL) was added and the mixture was stirred for additional 30 min. The organic phase was dried (magnesium sulfate), filtered and evaporated to yield 140 mg (98%) of the pure material as an oil.: $^1$H NMR (300 MHz, CDCl$_3$) δ (0.72, 1.15) (t, 3H) (1.10,1.21) (s, 9H). 2.35 (m, 2H), 2.84 (m, 4H), 3.52 (s, 2H), 3.67 (m, 1H), 6.9–7.4 (m, 8H) Shift values within parentheses indicate dual signals due to amide rotameric forms.; MS m/e 364 (M+, 11), 335 (100), 91 (33), 306 (19).

EXAMPLE 31

5-(2-propenyloxy)-2-(di-n-propylamino)-indan. (A-4, Chart A)

Sodium hydride (60 mg, 1.24 mmol) was washed with hexane twice, then suspended in DMF (3 mL) and stirred under nitrogen atmosphere. 5-hydroxy-2-n-propylamino) indan hydrobromide (Preparation 9, 100 mg, 0.31 mmol) dissolved in DMF (3 mL) was added and stirred for 45 min. Allyl bromide (0.034 mL, 0.4 mmol) was added and the reaction stirred overnight. Water was added and extracted with t-butyl methyl ether (3×30 mL). The combined organic layers were washed with water, brine, dried (Na$_2$SO$_4$), filtered and concentrated to yield an oil. The oil was chromatographed on 10 g silica gel, eluting with methylene chloride/methanol (9:1). Homogenous fractions were combined to yield the title compound as an oil (60%): $^1$H NMR (CDCl$_3$) δ 7.1–7.04 (m, 1H), 6.75–6.65 (m, 2H), 6.15–5.96 (m, 1H), 5.42–5.24 (m, 2H), 4.51–4.48 (m, 2H), 3.75–3.63 (m, 1H), 3.05–2.85 (m, 4H), 2.58–2.53 (m, 4H), 1.60–1.50 (m, 4H), 0.89 (t, J=7.3 Hz, 6H).

EXAMPLE 32

5,6 di-toluenesulfonyloxy-2-(di-n-propylamino)indan (A-5, Chart A)

To a solution of 5,6-di-hydroxy-2-(di-n-propylamino) indan (Preparation 10, 357 mg, 1.08 mmol) in methylene chloride (30 mL) was added dimethylaminopyridine (cat, 10 mg), triethylamine (0.9 mL, 6.48 mmol) and p-tosylchloride (1.12 g, 3.24 mmol) in methylene chloride. After 12 h, additional tosylchloride (1 g) and triethylamine (1 mL) was added. After 48 h, the reaction was quenched with water and extracted with methylene chloride (3×70 mL). The combined organic layers were washed with brine, dried (MgSO$_4$), filtered and evaporated to yield a brown oil (1.08 g). The oil was chromatographed using 300 g silica gel eluting with methylene chloride/methanol (19:1) to yield the title compound as an oil (520 mg, 86%). High resolution FAB MS: theory C$_{29}$H$_{35}$NS$_2$O$_6$+1H: 558.1984; observed: 558.2000.

EXAMPLE 33

5-methanesulfonyloxy-2-(di-n-propylamino)indan (A-5, Chart A)

To a solution of 5-hydroxy-2-(di-n-propylamino)indan hydrobromide (Preparation 9, 450 mg, 1.43 mmol) in methylene chloride (30 mL) and triethylamine (0.5 mL) at 0 C. was added mesyl chloride (0.144 mL, 1.9 mmol). After 18 h, water was added and the layers separated. The aq. layer was washed with methylene chloride (3×75 mL) and the combined organic layers were washed with brine, dried (MgSO$_4$), filtered and evaporated to yield a brown oil. The oil was chromatographed on 400 g silica gel, eluting with methylene chloride/methanol (19:1). Homogeneous fractions were combined to yield the title compound as a brown oil (280 mg): $^1$H NMR (CDCl$_3$) δ 7.20–7.01 (m, 3H), 3.73–3.68 (m, 1H), 3.12 (s, 3H), 3.09–2.94 (m, 4H), 2.54–2.49 (m, 4H), 1.55–1.47 (m, 4H), 0.89 (t, J=7.3 Hz, 6 H); high resolution FAB MS: theory for C$_{16}$H$_{25}$NO$_3$S+1H= 312.1633, observed: 312.1637.

EXAMPLE 34

5-Carbomethoxy-2-(di-n-propylamino)indan (A-6, Chart A)

The title compound was prepared from 5-(trifluoromethylsulfonyloxy)-2-(n-propylamino)indan (Example 2, 1 g, 2.7 mmol) using the Preparation outlined in Examples 9 and 10 to yield an oil (52%): MS m/e 275, 246, 175, 143, 131, 115; $^1$H NMR (CDCl$_3$) δ 7.84–7.21 (m, 3H), 3.89 (s, 3H), 3.68 (m, 1H), 3.10–3.0 (m, 4H), 1.53–1.46 (m, 4H), 0.8 (t, J=7.3 Hz, 6H).

EXAMPLE 35

5-Carboxamido-2-(di-n-propylamino)indan (A-6, Chart A)

A solution of 5-Carbomethoxy-2-(di-n-propylamino) indan (Example 34, 390 mg, 1.4 mmol) and formamide (0.196 mL, 5 mmol) was heated to 100 C. under argon. Sodium methoxide (0.5 mL) was added dropwise over 5 min. The reaction mixture was cooled to rt and 2-propanol added. the mixture was filtered and the filtrate concentrated to yield a brown solid. The solid was chromatographed on 350 g silica gel eluting with methylene chloride/methanol. Homogeneous fractions were combined to yield the title compound as an off-white solid: mp 88°–90° C.

EXAMPLE 36

5,6-Di-trifluomethansulfonyloxy-2-(propylamino)indan (A-5, Chart A).

In a vigorously stirred mixture of methylene chloride (25 mL) and aqueous sodium hydroxide (9 mL, 10%) was dissolved 5,6-di-hydroxy-2-(propylamino)indan (Preparation 18, 630 mg, 2.19 mmol). To this solution was then added N-phenyltrifluormethanesulfonimide (1.128 g, 3.16 mmol) and tetrabutylammonium sulfate (72 mg). The vigorous stirring was then maintained for 24 hours. The reaction mixture was quenched by the addition of dilute hydrochloric acid (15 mL, 10%), diethyl ether (50 mL) and finally water (50 mL). The aqueous layer was separated and the organic layer extracted with several portions of water. The combined aqueous extracts were then carefully basified to reach a pH of 9. The basic solution was then extracted with diethyl ether (3×50 mL). The combined extracts were dried (Na$_2$SO$_4$), filtered and the solvent removed to yield 175 mg of the crude product. This was chromatographed by flash chromatography eluting with methylene chloride/methanol (19:1) Homogenous fractions were combined to yield the title compound which was converted to the HCl salt and recrystallized form iso-propanol/iso propyl ether. mp 220°–225° C.

EXAMPLE 37

4-methyl-2-(di-n-propylamino)indan (A-3, Chart A)

The title compound was prepared following the procedure outlined in Preparation 7 using 4-methyl-2-aminoindan (Preparation 20) to yield an oil (320 mg, 40%) which was converted to the HCl salt and recrystallized from methanol/ethyl acetate: mp 180°–183° C.

EXAMPLE 38

4,5-di-methyl-2-(di-n-propylamino)indan (A-3, Chart A)

The compound was prepared following the procedure outlined in Preparation 7 using 6,7-di-methyl-2-aminoindan (Preparation 26) to yield the title compound (360 mg, 46%). The compound was converted into the HCl salt and recrystallized using ethyl acetate to yield a white solid: mp 184° C.

EXAMPLE 39

5,6-di-methyl-2-(di-n-propylamino)indan (A-3, Chart A)

The compound was prepared following the procedure outlined in Preparation 7 using 5,6-di-methyl-2-aminoindan (Preparation 27) to yield the title compound (420 mg, 46%). The compound was converted into the HCl salt and recrystallized using ether/ethyl acetate to yield a white solid: mp 182° C.

EXAMPLE 40

5-methyl-2-(di-n-propylamino)-indan (A-3, Chart A)

The compound was prepared following the procedure outlined in Preparation 7 using 6-methyl-2-aminoindan (Preparation 31) to yield the title compound (120 mg, 26%). The compound was converted into the HCl salt and recrystallized using hexane/ethyl acetate to yield a white solid: mp 153°–155° C.

EXAMPLE 41

4-Fluoro-2-(n-propyl)aminoindan (A-3, Chart A)

The compound was prepared following the procedure outlined in Preparation 7 using 4-fluoro-2-aminoindan (Preparation 31) to yield the title compound (80 mg, 10%). The compound was converted into the HCl salt and recrystallized using ethyl acetate to yield a white solid: mp 220°–222° C.

EXAMPLES 42 AND 43

5-(i-propyl)-2-(di-n-propylamino)indan and 5-(i-propyl)-2-(n-propylamino)indan (A-3, Chart A)

The compound was prepared following the procedure outlined in Preparation 7 using 5-(i-propyl)-2-aminoindan (Preparation 40) to yield 5-(i- propyl)-2-(di-n-propyl-amino) indan (120 mg, 26%). The compound was converted into the HCl salt and recrystallized using ether to yield a tan solid: mp 150–152 C. Also, 5-(i-propyl)-2- (n-propylamino)indan (100 mg, 22%) as an oil was collected. The compound was converted into the HCl salt and recrystallized using ethyl acetate to yield an off-white solid: mp 144°–147° C.

EXAMPLE 44

4,6-dimethyl-2-(di-n-propylamino)indan (A-3, Chart A).

The compound was prepared following the procedure outlined in Preparation 7 using 4,6-dimethyl-2-aminoindan (Preparation 44) to yield the title compound as a crude oil (420 mg).

EXAMPLE 45

4,7-dimethyl-2-(di-n-propylamino)indan (A-3, Chart A)

The compound was prepared following the procedure outlined in Preparation 7 using 4,7-dimethyl-2-aminoindan (Preparation 50) to yield the title compound as a crude oil (560 mg).

EXAMPLE 46

5-propyl-2-(di-n-propylamino)indan (A-3, Chart A)

The compound was prepared following the procedure outlined in Preparation 7 using 5-propyl-2-aminoindan (Preparation 55) to yield the title compound as a crude oil (620 mg).

EXAMPLE 47

5-(t-butyl)-2-(di-n-propylamino)indan (A-3, Chart A)

The compound was prepared following the procedure outlined in Preparation 7 using 5-(t-butyl)-2-aminoindan (Preparation 59) to yield the title compound as a crude oil (575 mg).

EXAMPLE 48

5-Trifluoromethyl-2-(di-n-propylamino)indan (C-2, Chart C)

A solution of 5-bromo-2-(di-n-propylamino)indan (Example 11), sodium trifluoroacetate, and copper (I) iodide in N-methylpyridone is heated at 160° C. for 4 h under nitrogen (*Chem Lett* 1981, 1719). The reaction mixture is cooled to room temperature and diluted with ethyl acetate. The mixture is filtered through a layer of Celite pad and the filtrate is washed with water, brine, dried ($MgSO_4$), filtered, and concentrated. The oil is purified by liquid chromatography to give the title compound as a yellow oil.

EXAMPLE 49

5-Sulfoxamido-2-(di-n-propylamino)indan (C-2, Chart C)

To a solution of 5-bromo-2-(di-n-propylamino)indan (Example 11) in THF is treated with sec-butyllithium in hexane at –78° C. under nitrogen. The mixture is allowed to warm to 0° C. over 30 min and cooled to –78° C. Dry sulfur dioxide gas is bubbled through the solution for 20 min. (*Organomet. Chem. Rev. Sect. A* 1970, 5, 281). After stirring the mixture under sulfur dioxide atmosphere at room temperature, the solvent is removed in vacuo. The residue is suspended in methylene chloride and excess thionyl chloride is added. The mixture is stirred for 1 h and the excess sulfuryl chloride and solvent is removed in vacuo. The residue is redissolved in methylene chloride and filtered. Then dry ammonia gas is bubbled through the filtrate. The precipitate is collected to give the title compound.

EXAMPLE 50

5-(3-Thiophene)-2-(di-n-propylamino)indan (C-2, Chart C)

To a solution of 5-trifluoromethanesulfonyloxy-2-(di-n-propylamino)indan (Example 2) in 1,4-dioxane is treated with bis(triphenylphosphine)palladium (II) chloride, triphenylphosphlne, lithium chloride, and 3-(tributylstannyl) thiophene under nitrogen. The reaction mixture is refluxed for 6 h (*J. Am. Chem. Soc.* 1987, 109, 5478; *Synthesis* 1980, 727). The crude product is purified by chromatography to afford the title compound.

EXAMPLE 51

5-Ethynyl-2-(di-n-propylamino)indan (C-2, Chart C)

To a solution of 5-trifluoromethanesulfonyloxy-2-(di-n-propylamino)indan (Example 2) in 1,4-dixoane is treated with tri-n-butylethynylstannane, lithium chloride, tetrakis (triphenylphosphlne)palladium(0), and a few crystals of 2,6-di-tert-butyl-4-methylphenol under nitrogen (*J. Am. Chem. Soc.* 1987, 109, 5478). The mixture is refluxed for 6 h, cooled to room temperature, and treated with pyridine and pyridine fluoride and iluted with diethyl ether. The resulting crude product is purified by chromatography to give the title compound.

EXAMPLE 52

5-Acetyl-2-(di-n-propylamino)indan (C-2, Chart C)

To a solution of 5-trifluoromethanesulfonyloxy-2-(di-n-propylamino)indan (Example 2) in DMF is treated sequentially with triethylamine, butyl vinyl ether, 1,3-bis (diphenylphosphino)propane, and palladium acetate under nitrogen. The mixture is heated at 80° C. for 0.5 h. (*J. Org. Chem.* 1990, 55 3654). The reaction mixture is cooled to room temperature and treated with 5% HCl. After stirring for 0.5 h, the mixture is extracted with methylene chloride. The crude product is purified by chromatography to yield the title compound.

EXAMPLE 53

5-Cyano-2-(di-n-propylamino)indan (C-2, Chart C)

To a solution of 5-carboxamido-2-(di-n-propylamino) indan (Example 35) in DMF is treated with phosphorus oxychloride under nitrogen. The solution is heated at 80° C. for 3 h (*J. Med. Chem.* 1968, 11, 322). The reaction ia quenched with 10% sodium hydroxide and extracted with methylene chloride. The crude product is purified by chromatography to give the title compound.

EXAMPLE 54

5-Carbomethoxy-6-acetoxy-2-(di-n-propylamino)indan (A-6, Chart A)

Following the general procedure of Example 9 and making non-critical variations but starting with 5-trifluoromethansulfonyloxy-6-acetoxy-2-(di-n-propylamino)indan (Example 8), the title compound is obtained.

EXAMPLE 55

5-Carbomethoxy-6-trifluromethanesulfonyloxy-2-(di-n-propylamino)indan (A-6, Chart A)

Following the general procedure of Example 3 and making non-critical variations but starting with 5-carbomethoxy-6-hydroxy-2-(di-n-propylamino)indan (Example 10), the title compound is obtained.

EXAMPLE 56

5-Trifluromethansulfonyloxy-6-methoxy-2-(di-n-propylamino)indan (A-6, Chart A)

A solution of 5-trifluoromethansulfonyloxy-6-hydroxy-2-(di-n-propylamino)indan (Example 7) in DMF is added to a suspension of sodium hydride in DMF under nitrogen. The mixture is alkylated with methyl iodide to yield the title compound.

EXAMPLE 57

5-Carbomethoxy-6-methoxy-2-(di-n-propylamino)indan (A-6, Chart A)

Following the general procedure of Example 9 and making non-critical variations but starting with 5-trifluoromethansulfonyloxy-6-methoxy-2-(di-n-propylamino)indan (Example 56), the title compound is obtained.

EXAMPLE 58

5-Formyl-6-methoxy-2-(di-n-propylamino)indan (A-6, Chart A)

A solution of 5-carbomethoxy-6-methoxy-2-(di-n-propylamino)indan (Example 57) in THF under nitrogen is treated with DIBAL-H at −78° C. After work-up and purification, the title compound is obtained.

EXAMPLE 59

5-Hydroxymethyl-6-methoxy-2-(di-n-propylamino)indan (A-6, Chart A)

A solution of 5-carbomethoxy-6-methoxy-2-(di-n-propylamino)indan (Example 57) in THF at 0° C. under nitrogen is treated with excess lithium aluminum hydride. After work-up and purification, the title compound is obtained.

EXAMPLE 60

5-Carboxy-6-methoxy-2-(di-n-propylamino)indan (A-6, Chart A)

A solution of 5-carbomethoxy-6-methoxy-2-(di-n-propylamino)indan (Example 57) in methanol/water is hydrolyzed with sodium hydroxide. After work-up and purification, the title compound is obtained.

EXAMPLE 61

5-Acetyl-6-methoxy-2-(di-n-propylamino)indan (A-6, Chart A)

Following the general procedure of Example 52 and making non-critical variations but starting with 5-trifluoromethanesulfonyloxy-6-methoxy-2-(di-n-propylamino)indan (Example 56), the title compound is obtained.

EXAMPLE 62

5-Carboxamido-6-methoxy-2-(di-n-propylamino)indan (A-6, Chart A)

Following the general procedure of Example 35 and making non-critical variations but starting with 5-carbomethoxy-6-methoxy-2-(di-n-propylamino)indan (Example 57), the title compound is obtained.

EXAMPLE 63

5-Ethynyl-6-methoxy-2-(di-n-propylamino)indan (A-6, Chart A)

Following the general procedure of Example 51 and making non-critical variations but starting with 5-trifluoromethanesulfonyloxy-6-methoxy-2-(di-n-propylamino)indan (Example 56), the title compound is obtained.

EXAMPLE 64

5-Cyano-6-methoxy-2-(di-n-propylamino)indan (A-6, Chart A)

Following the general procedure of Example 53 and making non-critical variations but starting with 5-carboxamido-6-methoxy-2-(di-n-propylamino)indan (Example 62), the title compound is obtained.

EXAMPLE 65

5,6-Di-(hydroxmethyl)-2-(di-n-propylamino)indan (A-6, Chart A)

Following the general procedure of Example 59 and making non-critical variations but starting with 5,6-dicarbomethoxy-2-(di-n-propylamino)indan (Example 9), the title compound is obtained.

EXAMPLE 66

5,6-Di-(methoxmethyl)-2-(di-n-propylamino)indan (A-6, Chart A)

Following the general procedure of Example 56 and making non-critical variations but starting with 5,6-di-(hydroxymethyl)-2-(di-n-propylamino)indan (Example 65), the title compound is obtained.

Binding Data for Examples:

Competition binding experiments employed eleven dilutions of test compounds competing with [$^3$H]-5-(dipropylamino)-5,6-dihydro-4H-imidazo(4,5,1-ij)quinolin-2(1H)-one (R-enantiomer) (62 Ci/mmol, 2 nM) and [$^3$H]-spiperone (107 Ci/mmol, 0.5 nM) for D2 and D3 binding sites, respectively. (Lahti, R. A., Eur. J. Pharmacol., 202, 289 (1991)) In each experiment, cloned mammalian receptors expressed in CHO-K1 cells were used. (Chio, C. L., Nature, 343, 266 (1990); and Huff, R. M., Mol. Pharmacol. (1993), in press). IC50 values were estimated by fitting the data to a one-site model by non-linear least squares minimization. Ki values were calculated with the Chen-Prushoff equation.

| Example # | D2 (Ki,nM) | D3 (ki,nM) |
|---|---|---|
| 2 | 350 | 31 |
| 3 | 367 | 16 |
| 10 | 121 | 6.5 |
| 17 | 108 | 3.7 |
| 32 | 291 | 45 |

Chart A:

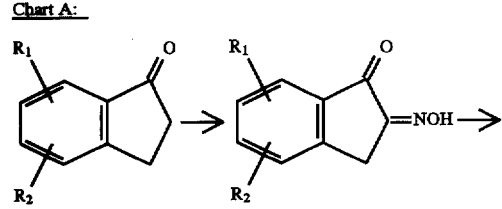

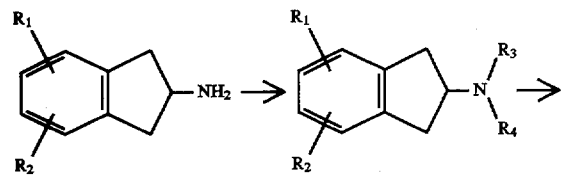

Chart A:

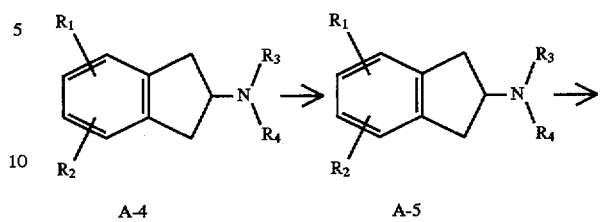

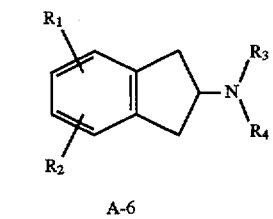

Chart B:

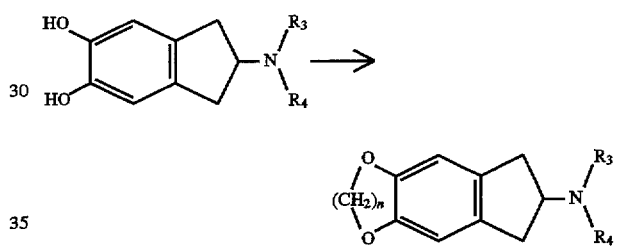

Chart C.

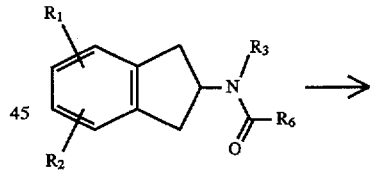

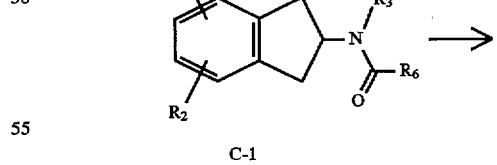

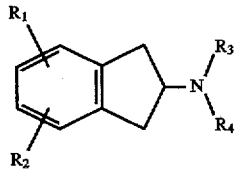

Chart D.

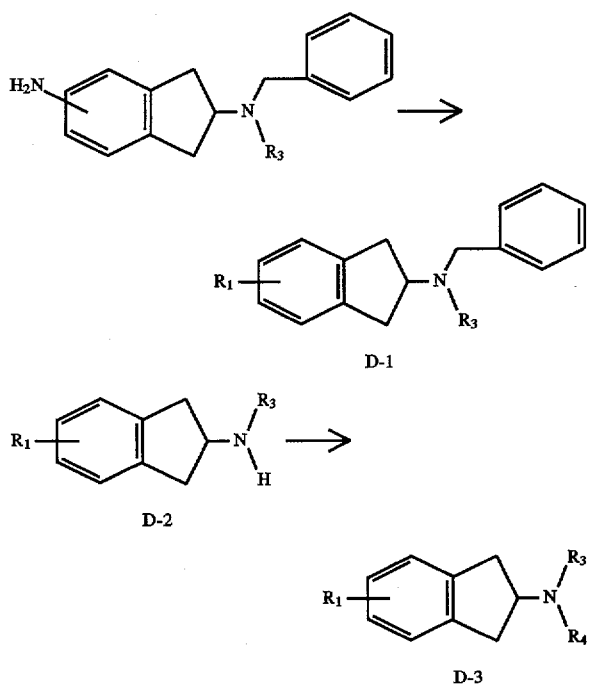

Chart E.

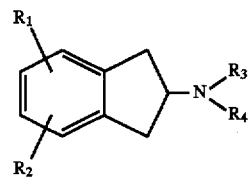

We claim:

1. A compound of Formula I and its pharmaceutically acceptable salts wherein $R_1$ and $R_2$ are independently chosen from hydrogen, $C_1$–$C_8$ alkyl, $OCH_3$, OH, $OSO_2CF_3$, $OSO_2CH_3$, $SOR_5$, $CO_2R_5$, $CONH_2$, $CONR_5R_6$, $COR_5$, CN, $SO_2NH_2$, $SO_2NR_5R_6$, $SO_2R_5$, —OCO—($C_1$–$C_6$ alkyl), —NCO—($C_1$–$C_6$ alkyl), —$CH_2O$—($C_1$–$C_6$ alkyl), —$CH_2OH$, —CO-Aryl, —$NHSO_2$-Aryl, —$NHSO_2$—($C_1$–$C_6$ alkyl), phthalimide, thiophenyl, pyrrol, pyrrolinyl, oxazolyl, provided that only one of $R_1$ and $R_2$ can be hydrogen or OH, or $R_1$ and $R_2$ together form —$O(CH_2)_{1-2}O$— or —$(CH_2)_{3-6}$—;

$R_3$ and $R_4$ are independently chosen $C_2$–$C_4$ alkenyl, $C_3$–$C_8$ alkynyl, $C_3$–$C_8$ cycloalkyl, —$(CH_2)_{1-4}$-thienyl, hydrogen or $C_1$–$C_8$ alkyl (except where $R_1$ or $R_2$ is hydrogen or OH or where both $R_1$ and $R_2$ are $OCH_3$ or a $C_1$–$C_8$ alkyl);

$R_5$ is hydrogen, $C_1$–$C_8$ alkyl, $C_2$–$C_4$ alkenyl, $C_3$–$C_8$ cycloalkyl; and $R_6$ is $C_1$–$C_8$ alkyl, $C_2$–$C_4$ alkenyl, $C_2$–$C_8$ alkynyl, $C_3$–$C_8$ cycloalkyl, or Aryl.

2. The compound of claim 1, wherein $R_1$ is $OSO_2CF_3$.
3. The compound of claim 2, wherein $R_2$ is $OSO_2CF_3$.
4. The compound of claim 1, wherein $R_3$ is propyl.
5. The compound of claim 4, wherein $R_4$ is propyl.
6. The compound of claim 1 which is a) 5,6-Methylenedioxy-2-(di-n-propylamino)indan, b) 5,6-Ethylenedioxy-2-(di-n-propylamino)indan, c) 5-(trifluoromethylsulfonyloxy)-2-(di-n-propylamino) indan, or d) 5,6-(di-trifluoromethylsulfonyloxy)-2-(di-n-propylamino)indan.

7. A method for treating a central nervous system disorder associated with dopamine D3 receptor activity comprising: administering to a patient in need thereof a therapeutically effective amount of a formula I compound of claim 1.

8. The method of claim 7, wherein the disorder is selected from schizophrenia, mania, depression, geriatric disorders, drug abuse and addiction, Parkinson's disease, sleep disorders, circadian rhythm disorders, anxiety disorders and dementia.

* * * * *